United States Patent
Hakimelahi

(10) Patent No.: US 6,825,348 B2
(45) Date of Patent: Nov. 30, 2004

(54) ANTIVIRAL COMPOUNDS

(75) Inventor: Gholam Hossein Hakimelahi, Taipei (TW)

(73) Assignee: Academia Sinica, Taipei (TW)

( * ) Notice: Subject to any disclaimer, the term of this patent is extended or adjusted under 35 U.S.C. 154(b) by 15 days.

(21) Appl. No.: 10/183,878

(22) Filed: Jun. 25, 2002

(65) Prior Publication Data

US 2004/0002475 A1 Jan. 1, 2004

(51) Int. Cl.[7] .............................................. C07D 473/00
(52) U.S. Cl. ....................................... 544/244; 544/277
(58) Field of Search ........................ 514/47, 263, 263.4, 514/79; 536/26.1; 544/244, 277

(56) References Cited

PUBLICATIONS

Hakimelahi et al "Design, Synthesis, and Biological Evaluation of Novel Nucleoside and Nucleotide Analogues as Agents against DNA Viruses and/or Retroviruses", J. Med. Chem. 2001, 44, 3710–3720.*

Balzarini, et al. *5–Phosphoribosyl 1–Pyrophosphate Synthetase Converts the Acyclic Nucleoside Phosphonates 9–(3–Hydroxy–2–phosphonylmethoxypropyl)adenine Directly to Their Antivirally Active Diphosphate Derivatives*. The Journal of Biological Chemistry 266(14): 8686–8689, May 15, 1991.

Singh, et al. *A Simple Solution to the Age Old Problem of Regioselective Functionalization of Guanine: First Practical Synthesis of Acyclic $N^9$—and/or $N^7$–Guanine Nucleosides Starting From $N^2$ ,$N^9$ –Diacetylguanine*. Journal of Organic Chemistry 64:4665–4668, 1999.

Keller, et al. *Enzymatic Phosphorylation of Acyclic Nucleoside Analogs and Correlations With Antiherpetic Activities*. Biochemical Pharmacology 30(22):3071–3077, 1981.

* cited by examiner

Primary Examiner—James O. Wilson
Assistant Examiner—Ganapathy Krishnan
(74) Attorney, Agent, or Firm—Fish & Richardson P.C.

(57) ABSTRACT

This invention relates to purine compounds of formula (I):

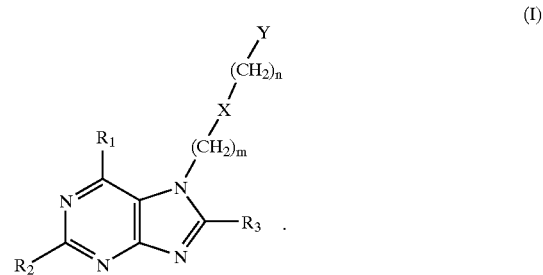

$R_1$ is $NH_2$ or OH; $R_2$ is H or $NH_2$; $R_3$ is H or alkyl; each of m and n, independently, is 1, 2, 3, or 4; X is O, S, or NH; and Y is H, halogen, $OR^a$, $P(O)(OR^a)_2$, or $P(O)(OR^a)(OR^b)$, in which $R^a$ is H, alkyl, aryl, heteroaryl, cyclyl, heterocyclyl, and $R^b$ is

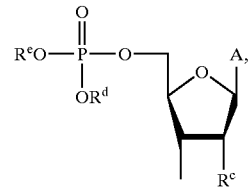

wherein A is adenine, guanine, cytosine, uracil, or thymine; $R^c$ is H or OH; $R^d$ is H or alkyl; $R^e$ is H, alkyl, or 5-ethylidene-(3,4-dialkoxyl)-furan-2-one; provided that if $R_1$ is $NH_2$, $R_2$ is H; and if $R_1$ is OH, $R_2$ is $NH_2$.

2 Claims, No Drawings

ANTIVIRAL COMPOUNDS

BACKGROUND

The DNA genome in the particle of a DNA virus can be double-stranded, single-stranded, or partially double-stranded DNA. *Papovaviridae* (e.g., papillomaviruses), *herpesviridae* (e.g., herpes simplex viruses), and *adenoviridae* (e.g., adenoviruses) contain double-stranded DNA genomes. Some viruses from *parvoviridae* (e.g., parvoviruses) contain single-stranded DNA as their genomes. Some viruses from *hepadnaviridae* (e.g., hepatitis B virus) contain partially double-stranded DNA as their genomes, and replicate their genomes through RNA intermediates. In contrast, retroviruses are a family of RNA viruses that replicate through a DNA intermediate. Examples of retroviruses include Moloney murine sarcoma viruses, human T-cell lymphotrophic viruses, human immunodeficiency viruses, and human foamy viruses.

Viruses described above cause a variety of diseases, such as the flu, common cold, herpes, measles, small pox, and encephalitis. Vaccination only offers protection for uninfected individuals for a few viral diseases. Thus, there is a need for identifying therapeutic agents useful for preventing or treating viral infection.

SUMMARY

The present invention is based, in part, on the discovery of nucleotide analogs that possess anti-viral activity.

In one aspect, this invention relates purine compounds of formula (I):

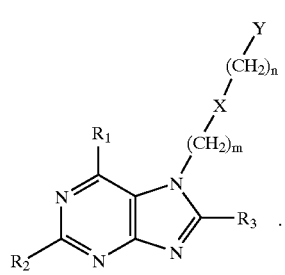

(I)

$R_1$ is $NH_2$ or OH; $R_2$ is H or $NH_2$; $R_3$ is H or alkyl; each of m and n, independently, is 1, 2, 3, or 4; X is O, S, or NH; and Y is H, halogen, $OR^a$, $P(O)(OR^a)_2$, or $P(O)(OR^a)(OR^b)$, in which $R^a$ is H, alkyl, aryl, heteroaryl, cyclyl, heterocyclyl, and $R^b$ is

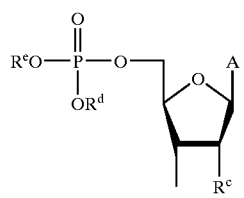

(referred to as "sugar-A($R^c$)—OP(O)($OR^d$)($OR^e$)" hereinafter), wherein A is adenine, guanine, cytosine, uracil, or thymine; $R^c$ is H or OH; $R^d$ is H or alkyl; $R^e$ is H, alkyl, or 5-ethylidene-(3,4-dialkoxyl)-furan-2-one; provided that if $R_1$ is $NH_2$, $R_2$ is H; and if $R_1$ is OH, $R_2$ is $NH_2$. Note that the left atom shown in any of the substituted groups set forth above is closest to the purine ring.

Referring to formula (I), a subset of the purine compounds are those in which each of $R_1$ is $NH_2$ and $R_2$ is H. In these compounds, $R_3$ can be H; X can be O; and each of m and n, independently, is 1 or 2. In some embodiments, m is 1, X is O, n is 2, and Y is $OR^a$, in which $R^a$ can be H. In other embodiments, m is 2, X is O, n is 1, and Y is $P(O)(OR^a)_2$, in which $R^a$ can be H. In still other embodiments, m is 2, X is O, n is 1, and Y is $P(O)(OR^a)(OR^b)$, in which $R^a$ can be H, and $R^b$ can be sugar-A($R^c$)—OP(O)($OR^d$)($OR^e$).

Another subset of the purine compounds of formula (I) are those in which $R_1$ is OH and $R_2$ is $NH_2$. In these compounds, $R_3$ can be H; X can be O; and each of m and n, independently, is 1 or 2. In some embodiments, m is 1, X is O, n is 2, and Y is $OR^a$, in which $R^a$ can be H. In other embodiments, m is 2, X is O, n is 1, and Y is $P(O)(OR^a)_2$, in which $R^a$ can be H. In still other embodiments, m is 2, X is O, n is 1, and Y is $P(O)(OR^a)(OR^b)$, in which $R^a$ can be H, and $R^b$ can be sugar-A($R^c$)-OP(O)($OR^d$)($OR^e$).

In another aspect, this invention encompasses purine compounds of formula (II):

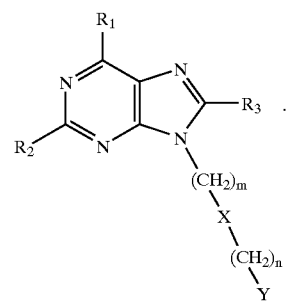

(II)

$R_1$ is $NH_2$ or OH; $R_2$ is H or $NH_2$; $R_3$ is H or alkyl; each of m and n, independently, is 1, 2, 3, or 4; X is O, S, or NH; and Y is $P(O)(OR^a)(OR^b)$, in which $R^a$ is H, alkyl, aryl, heteroaryl, cyclyl, heterocyclyl; and $R^b$ is 5-ethylidene-(3, 4-dialkoxy)-furan-2-one or sugar-A($R^c$)—OP(O)($OR^d$) ($OR^e$); wherein A is adenine, guanine, cytosine, uracil, or thymine; $R^c$ is H or OH; $R^d$ is H or alkyl; $R^e$ is H, alkyl, or 5-ethylidene-(3,4-dialkoxyl)-faran-2-one; provided that if $R_1$ is $NH_2$, $R_2$ is H; and if $R_1$ is OH, $R_2$ is $NH_2$.

Referring to formula (II), a subset of the purine compounds are those in which each of $R_1$ is $NH_2$ and $R_2$ is H. In these compounds, $R_3$ can be H; X can be O; and each of m and n, independently, is 1 or 2. In some embodiments, m is 2, X is O, n is 1, and Y is $P(O)(OR^a)(OR^b)$, in which $R^a$ can be H, and $R^b$ can be 5-ethylidene-(3,4-dialkoxy)-furan-2-one.

Another subset of the purine compounds of formula (II) are those in which $R_1$ is OH and $R_2$ is $NH_2$. In these compounds, $R_3$ can be H; X can be O; and each of m and n, independently, is 1 or 2. In some embodiments, m is 2, X is O, n is 1, and Y is $P(O)(OR^a)(OR^b)$, in which $R^a$ can be H, and $R^b$ can be 5-ethylidene-(3,4-dialkoxy)-furan-2-one.

Also within the scope of this invention is a method of preparing certain purine compounds of formula (I). The method includes reacting a compound of formula (III):

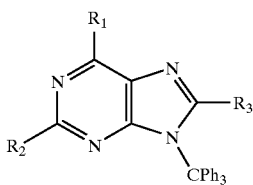

(III)

with an alkyl-X—(CH$_2$) halide to obtain a compound of formula (IV):

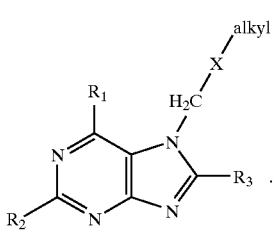

(IV)

In formulae (III) and (IV), R$_1$ is NH$_2$ or OH; R$_2$ is H or NH$_2$; R$_3$ is H or alkyl; and X is O, S, or NH; provided that if R$_1$ is NH$_2$, R$_2$ is H; and if R$_1$ is OH, R$_2$ is NH$_2$.

Unless specifically pointed out, alkyl, aryl, heteroaryl, cyclyl, heterocyclyl, adenine, guanine, cytosine, uracil, and thymine mentioned above include both substituted and unsubstituted moieties. The term "substituted" refers to one or more substituents (which may be the same or different), each replacing a hydrogen atom. Examples of substituents include, but are not limited to, halogen, cyano, nitro, hydroxyl, amino, mercapto, C$_1$~C$_6$ alkyl, C$_1$~C$_6$ alkenyl, C$_1$~C$_6$ alkynyl, aryl, heteroaryl, C$_4$~C$_8$ cyclyl, C$_4$~C$_8$ heterocyclyl, alkyloxy, aryloxy, alksulfanyl, arylsulfanyl, alkylamino, arylamino, dialkylamino, diarylamino, alkylcarbonyl, arylcarbonyl, heteroarylcarbonyl, alkylcarboxyl, arylcarboxyl, heteroarylcarboxyl, alkyloxycarbonyl, aryloxycarbonyl, heteroaryloxycarbonyl, alkylcarbamido, arylcarbamido, heterocarbamido, alkylcarbamyl, arylcarbamyl, heterocarbamyl, wherein each of alkyl (including alk), alkenyl, aryl, heteroaryl, cyclyl, and heterocyclyl is optionally substituted with halogen, cyano, nitro, hydroxyl, amino, mercapto, C$_1$~C$_6$ alkyl, aryl, heteroaryl, alkyloxy, aryloxy, alkylcarbonyl, arylcarbonyl, alkylcarboxyl, arylcarboxyl, alkyloxycarbonyl, or aryloxycarbonyl.

The term "alkyl" refers to both linear and branched alkyl. The term "cyclyl" refers to a hydrocarbon ring containing 4 to 8 carbons. The term "heterocyclyl" refers to a ring containing 4 to 8 ring members that have at least one heteroatom (e.g., S, N, or O) as part of the ring. The term "aryl" refers to a hydrocarbon ring system having at least one aromatic ring. Examples of aryl moieties include, but are not limited to, phenyl, naphthyl, and pyrenyl. The term "heteroaryl" refers to a hydrocarbon ring system having at least one aromatic ring which contains at least one heteroatom such as O, N, or S. Examples of heteroaryl moieties include, but are not limited to, furyl, pyrrolyl, thienyl, oxazolyl, imidazolyl, thiazolyl, pyridinyl, pyrimidinyl, quinazolinyl, and indolyl.

All of the purine compounds described above include the compounds themselves, as well as their salts. The salts, for example, can be formed between a positively charged substituent (e.g., amino) on a compound and an anion. Suitable anions include, but are not limited to, chloride, bromide, iodide, sulfate, nitrate, phosphate, citrate, methanesulfonate, trifluoroacetate, and acetate. Likewise, a negatively charged substituent (e.g., carboxylate) on a compound can form a salt with a cation. Suitable cations include, but are not limited to, sodium ion, potassium ion, magnesium ion, calcium ion, and an ammonium cation such as teteramethylammonium ion.

In addition, some of the just-described purine compounds have one or more double bonds, or one or more asymmetric centers. Such compounds can occur as racemates, racemic mixtures, single enantiomers, individual diastereomers, diastereomeric mixtures, and cis- or trans- or E- or Z- double bond isomeric forms.

Exemplary purine compounds of formula (I) and (II) include:

(compound 9)

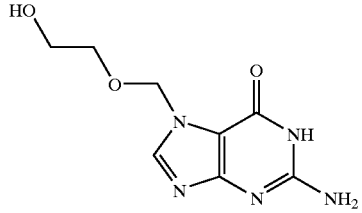

(compound 14)

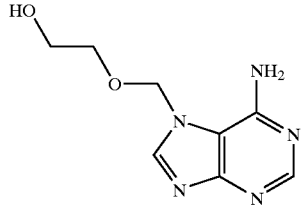

(compound 20)

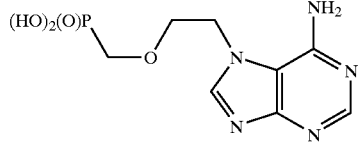

(compound 24)

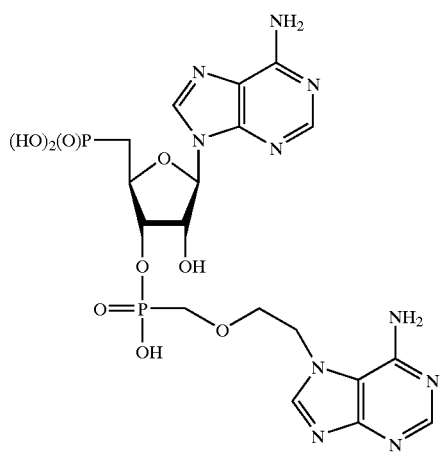

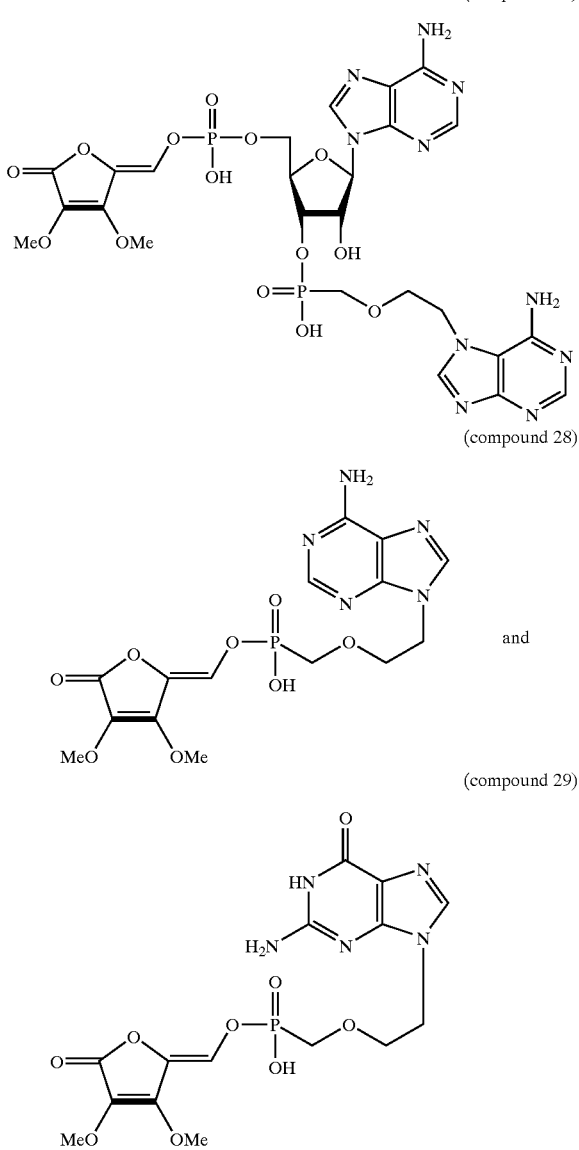

(compound 25)

(compound 28)

and (compound 29)

This invention also features a method of treating infection by virus. The method includes administering to a subject in need thereof an effective amount of a purine compound of formula (I) or formula (II) as described above. Examples of the viruses include DNA viruses such as herpesviridae (e.g., herpes simplex viruses) and retroviruses such as Moloney murine sarcoma viruses and human immunodeficiency viruses (e.g., human immunodeficiency viruses-1 or -2).

As used herein, the term "treating infection" refers to use of one or more purine compounds described above for preventing or treating infection by virus, or other disease states secondary to viral infection, e.g., cervical cancer induced by Papilovirus.

Also within the scope of this invention are a composition containing one or more of the aforementioned purine compounds for use in treating viral infection, and the use of such a composition for the manufacture of a medicament for infection treatment.

Other features or advantages of the present invention will be apparent from the following detailed description of several embodiments, and also from the appending claims.

DETAILED DESCRIPTION

This invention relates to the purine compounds of formula (I) and formula (II) as described in the Summary section.

As shown in Scheme 1a below, the purine compounds of formula (I) can be prepared by a novel procedure: alkylation of $N^9$-tritylated purine compounds (III), followed by concomitant self-detritylation to yield the desired $N^7$-alkylated purine nucleosides (IV). In this Scheme, $R_1$, $R_2$, $R_3$, and X are defined in the Summary section.

Scheme 1a

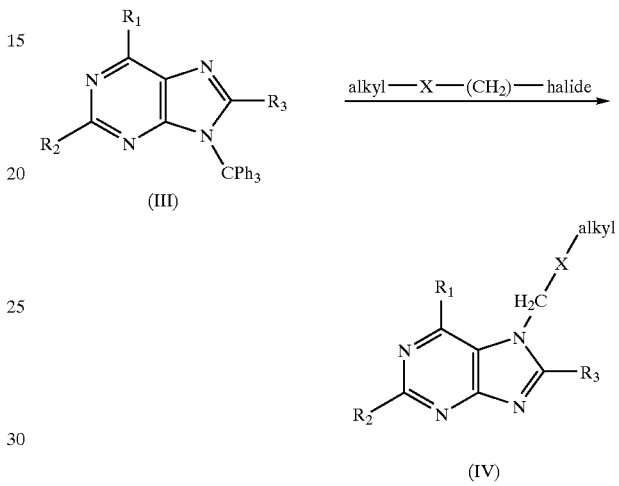

Compound (III) can be obtained by silylation of a purine (e.g., guanine) with hexamethyldisilazane in the presence of a catalytic amount of $(NH_4)_2SO_4$ at an elevated temperature, followed by condensation of the resultant silylated purine with trityl chloride.

Other than the just-described procedure, the purine compounds of formula (I) and formula (II) can be prepared by methods well known in the art. Scheme 1b shown below adepicts synthesis of the compounds of formula (I). In this scheme, $R_1$, $R_2$, $R_3$, m, n, X, and Y are defined in the Summary section.

Scheme 1b

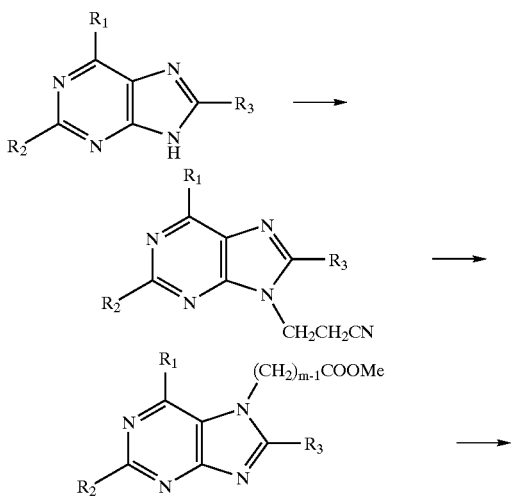

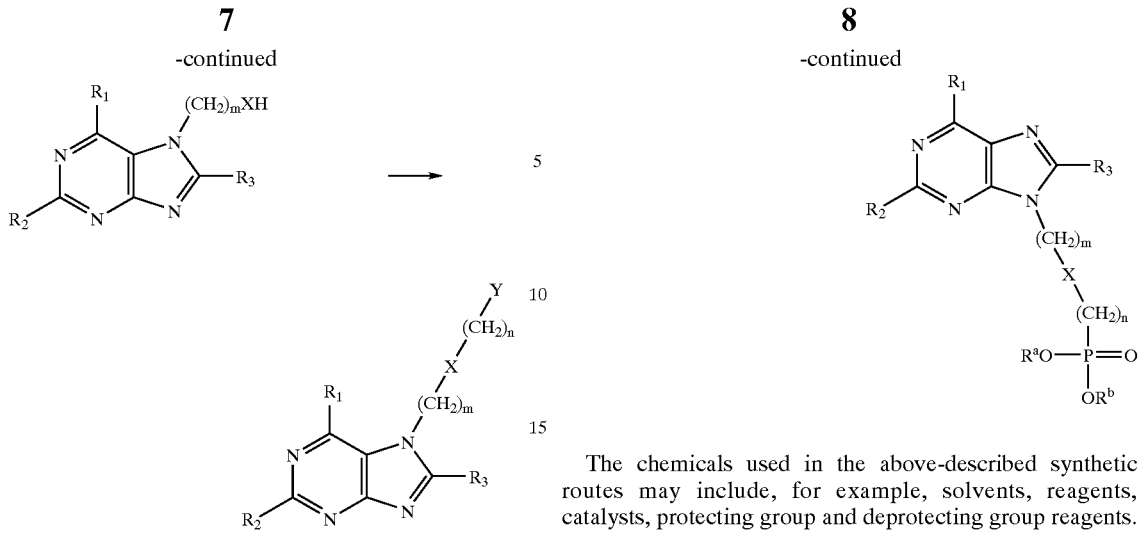

More specifically, a purine compound is alkylated with 3-bromopropionitrile in the presence of NaH to give $N^9$-cyanoethyl purine intermediate. Reaction of this intermediate with a methyliodo-ester and lithium 2,2,6,6-tetramethylpiperidine affords a mixture of $N^7$-alkylated and $N^9$-alkylated ester-containing products. Reduction of the ester in $N^9$-alkylated product gives another intermediate, which is converted to a desired purine compound of formula (I) by an alkylation reaction or by reacting with a phosphonate in the presence of tert-butoxide. Similarly, reduction of the ester in $N^7$-alkylated product gives a compound, which reacts with a phosphonate to produce an $N^7$-substituted phosphonate-purine.

Reaction of the $N^7$-substituted phosphonate-purine with a halide in the presence of $NaHCO_3$ affords a desired compound of formula (II).

Scheme 1c below depicts synthesis of the compounds of formula (II). In this scheme, $R_1$, $R_2$, $R_3$, $R^a$, $R^b$, m, n, X, and Y are defined in the Summary section.

Scheme 1c

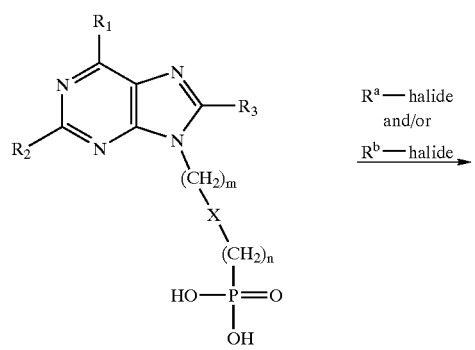

$R^a$ — halide
and/or
$R^b$ — halide

The chemicals used in the above-described synthetic routes may include, for example, solvents, reagents, catalysts, protecting group and deprotecting group reagents.

The methods described above may also additionally include steps, either before or after the steps described specifically herein, to add or remove suitable protecting groups in order to ultimately allow synthesis of the purine compound. In addition, various synthetic steps may be performed in an alternate sequence or order to give the desired compounds. Synthetic chemistry transformations and protecting group methodologies (protection and deprotection) useful in synthesizing applicable purine compounds are known in the art and include, for example, those described in R. Larock, *Comprehensive Organic Transformations*, VCH Publishers (1989); T. W. Greene and P. G. M. Wuts, *Protective Groups in Organic Synthesis*, $2^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

A purine compound thus synthesized can be further purified by a method such as column chromatography, high pressure liquid chromatography, or recrystallization.

Also within the scope of this invention is a pharmaceutical composition that contains an effective amount of at least one purine compound of the present invention and a pharmaceutically acceptable carrier. Further, this invention covers a method of administering to a subject in need of treating viral infection an effective amount of one or more of the purine compounds. The term "treating" is defined as the application or administration of a composition including the purine compound to a subject, who has a viral infection, a symptom of the infection, a disease or disorder secondary to the infection, or a predisposition toward the infection, with the purpose to cure, alleviate, relieve, remedy, or ameliorate the infection, the symptom of the infection, the disease or disorder secondary to the infection, or the predisposition toward the infection. "An effective amount" is defined as the amount of the purine compound which, upon administration to a subject in need thereof, is required to confer therapeutic effect on the subject. An effective amount of the purine compound may range from 5 mg/Kg to 20 mg/Kg. Effective doses also vary, as recognized by those skilled in the art, depending on route of administration, excipient usage, and the possibility of co-usage with any other therapeutic agent, such as an antiviral agent.

To practice the method of the present invention, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. A purine compound-containing composition can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form specific, more soluble complexes with the indole compounds, or one or more solubilizing agents, can be utilized as pharmaceutical excipients for delivery of the purine compounds. Examples of other carriers include colloidal silicon dioxide, magnesium stearate, cellulose, sodium lauryl sulfate, and D&C Yellow #10.

A purine compound of this invention can be preliminarily screened for its efficacy in treating viral infection by one or more of the following in vitro assays.

In one assay, a purine compound is tested for its inhibition of cytopathogenicity against the herpes simplex type 1 virus, herpes simplex simplex type 2 virus, thymidine kinase-positive and thymidine kinase-deficient strains of varicell-zoster virus, or human cytomegalovirus in Vero cells. The method for measuring viruses-induced cytophogenicity in Vero cell cultures, as well as the toxicity of the test compound toward HeLa and Vero cells, has been described in e.g., De Clercq et al. (1980) *J. Infect. Dis.* 141: 563–574.

In another assay, a purine compound is tested for its inhibition of cytopathogenicity against the human immunodeficiency viruses HIV-1 (IIIB) and HIV-2 (LAV-2) in MT4 cells. The method for measuring viruses-induced cytophogenicity in MT4 cells or CEM cells, as well as the toxicity toward MT4 and CEM cells, has been described in e.g., Averett, (1989) *J. Virol. Methods* 23: 263–276.

The antiviral activity of a purine compound can be further assessed using an in vivo animal model. See the specific examples below.

Without further elaboration, it is believed that the above description has adequately enabled the present invention. The following specific embodiments are, therefore, to be construed as merely illustrative, and not limitative of the remainder of the disclosure in any way whatsoever. All of the publications cited herein are hereby incorporated by reference in their entirety.

General. For anhydrous reactions, glassware was dried overnight in an oven at 120° C. and cooled in a desiccator over anhydrous $CaSO_4$ or silica gel. Reagents were purchased from Fluka and enzymes from Sigma Chemical Co. Solvents, including dry ether and tetrahydrofuran (THF), were obtained by distillation from the sodium ketyl of benzophenone under nitrogen. Other solvents, including chloroform, dichloromethane, ethyl acetate, and hexanes were distilled over $CaH_2$ under nitrogen. Absolute methanol and ethanol were purchased from Merck and used as received.

Melting points were obtained with a Büchi 510 melting point apparatus. Infrared (IR) spectra were recorded on a Beckman IR-8 spectrophotometer. The wavenumbers reported are referenced to the 1601 $cm^{-1}$ absorption of polystyrene. Proton NMR spectra were obtained on a Varian XL-300 (300 MHz) Spectrometer. Chloroform-d and dimethylsulfoxide-$d_6$ were used as solvent; $Me_4Si$ ($\delta$ 0.00 ppm) was used as an internal standard. All NMR chemical shifts are reported as 6 values in parts per million (ppm) and coupling constants (J) are given in hertz (Hz). The splitting pattern abbreviations are as follows: s, singlet; d, doublet; t, triplet; q, quartet; br, broad; m, unresolved multiplet due to the field strength of the instrument; and dd, doublet of doublets. UV spectroscopy was carried out using an HP8452A diode array spectrophotometer. Mass spectra were carried out on a VG 70-250 S mass spectrometer. Microanalyses were performed on a Perkin-Elmer 240-B microanalyzer.

Purification on silica gel refers to gravity column chromatography on Merck Silica Gel 60 (particle size 230–400 mesh). Analytical TLC was performed on precoated plates purchased from Merck (Silica Gel 60 $F_{254}$). Compounds were visualized by use of UV light, $I_2$ vapor, or 2.5% phosphomolybdic acid in ethanol with heating.

9-[(2-Hydroxyethoxy)methyl]adenine 1,9-[(2-hydroxyethoxy)methyl]guanine (acyclovir 2), 9-(β-D-arabinofaranosyl)adenine (ara-A 3), 9-[2-(phosphonomethoxy)ethyl]adenine (PMEA 4) were used for comparison in Examples 8–10. Compounds 9, 14, 20, 24, 25, 28, and 29 were prepared by the methods described in Examples 1–7.

EXAMPLE 1

Synthesis of Compound 9

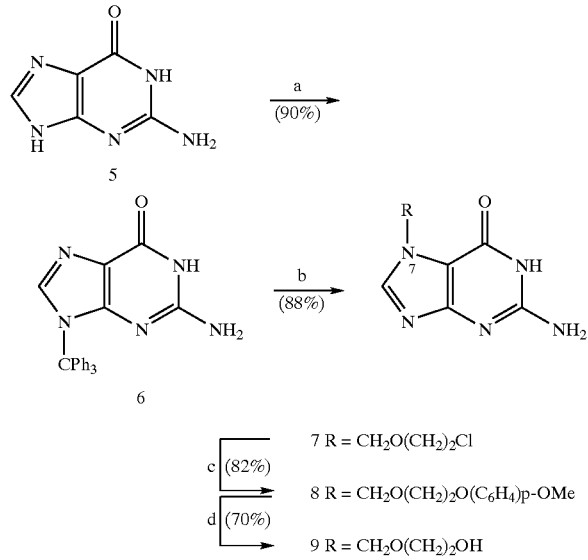

Scheme 2[a]

7 R = CH$_2$O(CH$_2$)$_2$Cl c (82%)

8 R = CH$_2$O(CH$_2$)$_2$O(C$_6$H$_4$)p-OMe d (70%)

9 R = CH$_2$O(CH$_2$)$_2$OH

[a] Reagents and conditions: (a) (1) Me$_2$SiNHSiMe$_3$, (NH$_4$)$_2$SO$_4$ (cat.) Δ, 24 h; (2) Ph$_3$CCl, MeCN, 25° C., 7.0 h. (b) Cl(CH$_2$)$_2$OCH$_2$Cl, DMF, 25° C., 8.0 h. (c) p-MeO(C$_6$H$_4$)O(CH$_2$)$_2$OCH$_2$Cl, DMF, 25° C., 8.0 h. (d) CAN, MeCN/H$_2$O (3:1), 0–25° C., 1.0 h.

As shown in Scheme 2, N$^9$-tritylated guanine 6 was synthesized in two steps. Silylation of guanine 5 with hexamethyldisilazane (HMDS) in the presence of a catalytic amount of (NH$_4$)$_2$SO$_4$ at refluxing temperature followed by condensation of the resultant silylated guanine with trityl chloride in MeCN at 25° C. afforded the desired N$^9$-tritylated guanine 6 in 90% yield. Treatment of 6 with (chloroethoxy)methyl chloride (Hakimelahi & Khalafi-Nezhad (1989) *Helv. Chim. Acta* 72: 1495–1550) in DMF at room temperature gave the corresponding N$^7$-alkylated guanine 7 in 88% yield. Likewise, treatment of 6 with [2-(p-methoxyphenyloxy)ethoxy]methyl chloride (Khorshidi (1986) Doctoral Thesis in Pharmacy, Faculty of Medicine, Isfahan University, Isfahan, Iran) led to the N$^7$-isomer 8 in 82% yield. Removal of the p-methoxyphenyl moiety was then achieved by treatment with ceric ammonium nitrate (CAN, Fukuyama et al. (1985) *Tetrahedron Lett.* 26: 6291–6292) in a mixture of MeCN and H$_2$O (3:1) at 0–25° C. to afford compound 9 in 70% yield. For compound 9 (i.e., a N$^7$-isomer) and its corresponding N$^9$-isomer, their $^1$H and $^{13}$C NMR spectra are different. See, e.g., Kjellberg & Johansson (1986) *Tetrahedron* 42: 6541–6544; Shiragami et al. (1995) *Nucleosides & Nucleotides* 14: 337–340; and Bailey & Hamden (1987) *Nucleosides & Nucleotides* 6: 555–574. The $^1$H signals of H$_2$C(1') (5.81 ppm) and HC(8) (8.67 ppm) for the N$^7$-isomer were found to be shifted downfield relative to the corresponding signals of the N$^9$-isomer, in which the H$_2$C(1') and HC(8) resonated at 5.35 and 7.81 ppm, respectively. On the other hand, the $^1$H signals for NH$_2$ was observed to be shifted upfield for the N$^7$-isomer, 5.96 ppm for the N$^7$-isomer, relative to the corresponding signal for N$^9$-isomer, which was observed at 6.52 ppm. The $^{13}$C NMR signals for C(1') (75.25 ppm) and C(8) (143.92 ppm) of the N$^7$-isomer were found to be shifted downfield relative to the corresponding signals of the N$^9$-isomer, which were observed respectively at 71.64 and 137.89 ppm. In contrast, the signal of C(5) of the N$^7$-isomer resonated at 107.16 ppm, which was upper field to that of the N$^9$-isomer at 116.52 ppm. The UV $\lambda_{max}$ of the N$^7$-isomer appeared at 289 nm, whereas the corresponding $\lambda_{max}$ of the N$^9$-isomer appeared at 253 and 273 (sh) nm.

9-(Triphenylmethyl)guanine 6. Guanine 5 (1.51 g, 9.99 mmol) and (NH$_4$)$_2$SO$_4$ (100 mg) were suspended in HMDS (150 mL) and refluxed for 24 h. The solvent was evaporated under reduced pressure and the residue was dissolved in CH$_3$CN (150 mL). Triphenylmethyl chloride (2.79 g, 10.0 mmol) was added and the reaction mixture was stirred at 25° C. for 7.0 h. The solution was concentrated under reduced pressure and the residue was purified by use of column chromatography (hexanes/EtOAc=1.5:8.5) to afford 6 (3.54 g, 8.99 mmol) in 90% yield: mp 268–270° C.; R$_f$(hexanes/EtOAc=1:2) 0.34; UV (EtOH) $\lambda_{max}$ 254 (ε 13,870), 278 (sh); $^1$H NMR (DMSO-d$_6$) δ 5.97 (s, 2 H, NH$_2$), 7.09–7.39 (m, 16 H, HC$_8$+C(C$_6$H$_5$)$_3$), 10.45 (br s, 1H, NH); MS m/z 393 (M$^+$). Anal. (C$_{24}$H$_{19}$N$_5$O) C, H, N; calcd (%): 73.26, 4.87, 17.80; found (%): 73.20, 4.81, 17.78.

7-[(2-Chloroethoxy)methyl]guanine 7. To a solution of 6 (1.77 g, 4.49 mmol) in DMF (30 mL) was added (2-chloroethoxy)methyl chloride (0.65 g, 5.0 mmol). The reaction mixture was stirred at 25° C. for 8.0 h. The solution was then partitioned between EtOAc (100 mL) and water (100 mL). The EtOAc solution was washed with water (4×100 mL); then it was dried over MgSO$_4$ (s) and filtered. Evaporation under reduced pressure and purification of the residue by use of column chromatography (EtOAc) afforded 7 (1.07 g, 4.39 mmol) in 88%: mp>280° C. (dec.); R$_f$(hexanes/EtOAc=1:2) 0.20; UV (EtOH) $\lambda_{max}$ 288 (ε 15,100); $^1$H NMR (DMSO-d$_6$) δ 3.67 (t, J=6.10 Hz, 2 H, CH$_2$Cl), 3.75 (t, J=6.10 Hz, 2 H, OCH$_2$), 5.62 (s, 2 H, H$_2$C$_{1'}$), 6.15 (s, 2 H, NH$_2$), 7.58 (s, 1 H, NH), 8.16 (s, 1 H, HC$_8$); $^{13}$C NMR (DMSO-d$_6$) δ 43.39 (CH$_2$Cl), 68.50 (OCH$_2$) 74.71 (C$_{1'}$), 107.71 (C$_5$), 143.87 (C$_8$), 153.15 (C$_4$), 154.37 (C$_2$), 159.12 (C$_6$); MS m/z 243 (M$^+$, Cl-cluster). Anal (C$_8$H$_{10}$ClN$_5$O$_2$) C, H, N, Cl; calcd (%): 39.43, 4.14, 28.74, 14.56; found (%): 39.38, 4.13, 28.70, 14.45.

7-[(2-(p-Methoxyphenyloxy)ethoxy)methyl]guanine 8. Compound 8 (2.72 g, 8.20 mmol) was prepared in 82% yield from 6 (3.64 g, 9.25 mmol) and (2-(p-methoxyphenyloxy) ethoxy)methyl chloride (2.18 g, 10.1 mmol) in DMF (100 mL) by the method used for the synthesis of 7: mp>250° C. (dec.); R$_f$(hexanes/EtOAc=1:2) 0.18; UV (EtOH) $\lambda_{max}$ 290 (ε 16,500); $^1$H NMR (DMSO-d$_6$) δ 3.70 (s, 3 H, OCH$_3$), 4.02–4.10 (m, 4 H, O(CH$_2$)$_2$O), 5.74 (s, 2 H, H$_2$C$_{1'}$), 5.88 (s, 2 H, NH$_2$), 6.67, 6.70 (AA'BB', J=9.30 Hz, 4 H, C$_6$H$_4$), 7.50 (s, 1 H, NH), 8.85 (s, 1 H, HC$_8$); $^{13}$C NMR (DMSO-d$_6$) δ 56.12 (CH$_3$), 68.74 (OCH$_2$), 70.20 (CH$_2$Oph), 75.31(C$_{1'}$), 107.25 (C$_5$), 144.02 (C$_8$), 153.25 (C$_4$), 154.48 (C$_2$), 159.26 (C$_6$), 115.55, 116.38, 153.51, 155.56 (C$_6$H$_4$); MS m/z 331 (M$^+$). Anal (C$_{15}$H$_{17}$N$_5$O$_4$) C, H, N; calcd (%): 54.37, 5.17, 21.13; found (%): 54.26, 5.20, 21.19.

7-[(2-Hydroxyethoxy)methyl]guanine 9. To a solution of 8 (1.36 g, 4.10 mmol) in a mixture of CH$_3$CN (30 mL) and water (10 mL) was added CAN (2.25 g, 4.10 mmol) at 0° C. The stirred reaction mixture was allowed to warm-up to 25° C. within 1.0 h. Water (30 mL) was added to afford a solid. Filtration and crystallization of the solid from EtOH/water (4:1) gave 9 (0.65 g, 2.88 mmol) in 70% yield: mp>280° C. (dec.); R$_f$(hexanes/EtOAc=1:2) 0.08; UV (EtOH) $\lambda_{max}$ 289 (ε 16,000); $^1$H NMR (DMSO-d$_6$) δ 3.61–3.82 (m, 4H, O(CH$_2$)$_2$O), 4.85 (br s, 1H, OH), 5.81 (s, 2 H, H$_2$C$_{1'}$), 5.96 (br s, 2 H, NH$_2$), 6.61 (s, 1 H, NH), 8.67 (s, 1 H, HC$_8$); $^{13}$C NMR (DMSO-d$_6$) δ 60.91 (CH$_2$OH), 70.01 (OCH$_2$) 75.25

($C_{1'}$), 107.16 ($C_5$), 143.92 ($C_8$), 153.20 ($C_4$), 154.40 ($C_2$), 159.30 ($C_6$); MS m/z 225 (M$^+$). Anal ($C_8H_{11}N_5O_3$) C, H, N; calcd (%): 42.66, 4.92, 31.10; found (%): 42.75, 4.84, 31.21.

EXAMPLE 2

Synthesis of Compound 14

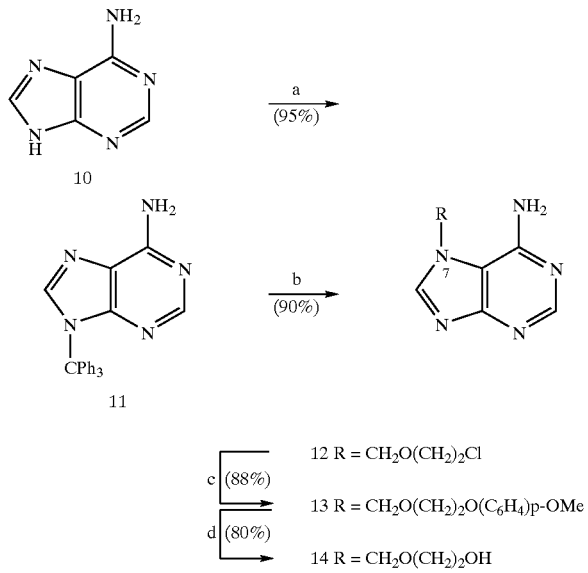

Scheme 3$^a$ $^a$ Reagents and conditions: (a) Ph$_3$CCl, pyridine/DMF (3:1), 25 ° C., 7.0 h. (b) Cl(CH$_2$)$_2$OCH$_2$Cl, CH$_2$Cl$_2$, 25° C., 8.0 h.
(c) pMeO(C$_6$H$_4$)—O(CH$_2$)$_2$OCH$_2$Cl, CH$_2$Cl$_2$, 25° C., 10 h.
(d) CAN, MeCN/H$_2$O (3:1), 0–25° C., 1.0 h.

As shown in Scheme 3, by the same synthetic strategy shown in Scheme 2, novel N$^7$-alkylated adenines 12 and 14 were obtained from adenine 10 via the N$^9$-tritylated adenine 11. Reaction of 11 with (2-chloroethoxy)methyl chloride in CH$_2$Cl$_2$ at 25° C. gave N$^7$-adenine derivative 12 in 90% yield. Likewise, reaction of 11 with [2-(p-methoxyphenyloxy)ethoxy]methyl chloride in CH$_2$Cl$_2$ at 25° C. gave N$^7$-isomer 13 in 86% yield. Treatment of 13 with CAN then produced the deprotected compound 14 in 80% yield.

For compound 14 (i.e., a N$^7$-isomer) and its corresponding N$^9$-isomer, their $^1$H and $^{13}$C NMR spectra are different. In methanol-d$_4$, pronounced downfield shifts were observed for the signals resulting from the H$_2$C(1') (5.79 ppm) and HC(8) (8.60 ppm) of the N$^7$-isomer when compared with those of the N$^9$-isomer, respectively observed at 5.67 and 8.27 ppm. In DMSO-d$_6$, the NH$_2$ signals of the N$^7$-isomer was shifted downfield to ~9.2 and 110.0 ppm, whereas the corresponding signals of the N$^9$-isomer appeared as a broad peak at ~7.3 ppm. The $^{13}$C NMR signals for C(1') (82.01 ppm) and C(8) (147.68 ppm) for the N$^7$-isomer were found to be shifted downfield relative to those of the N$^9$-isomer which were observed respectively at 74.31 and 143.14 ppm. The signals of the C(2) (144.29 ppm) and C(6) (152.12 ppm) for the N$^7$-isomer, however, were found to be shifted upfield relative to those of the N$^9$-isomer, observed respectively at 153.74 and 157.19 ppm. Furthermore, the H—C(2) coupling constants for the N$^7$- and N$^9$-isomers were respectively 220 and 204 Hz, whereas the corresponding H—C(8) coupling constants were respectively 224 and 217 Hz. The attachment of the side chain at the N-7 position of adenine was confirmed by HMQC spectroscopy, in which the H$_2$C(1') and C(6) exhibited a strong interaction in the N$^7$-isomer whereas the corresponding N$^9$-isomer showed long-range coupling between H$_2$C(1') and C(4).

9-(Triphenylmethyl)adenine 11. To a solution of 10 (1.35 g, 9.99 mmol) and DMF (10 mL) in pyridine (30 mL) was added Ph$_3$Cl (2.79 g, 10.0 mmol). The reaction mixture was stirred at 25° C. for 7.0 h. It was then diluted with EtOAc (150 mL) and water (100 mL). The organic layer was separated and then washed with water (4×100 mL). It was dried over MgSO$_4$ (s) and concentrated under reduced pressure to yield a foam. Purification was carried out by use of column chromatography (EtOAc/hexanes=8:2) to afford compound 11 (3.58 g, 9.48 mmol) in 95% yield: mp 260–262° C.; R$_f$(hexanes/EtOAc=1:2) 0.38; UV (EtOH) $\lambda_{max}$ 260 ($\epsilon$ 14,600); $^1$H NMR (CDCl$_3$) $\delta$ 5.60 (s, 2 H, NH$_2$), 7.15–7.31 (m, 15 H, C(C$_6$H$_5$)$_3$), 7.74 (s, 1 H, HC$_2$), 8.05 (s, 1 H, HC$_8$); MS m/z 377 (M$^+$); Anal. (C$_{24}$H$_{19}$N$_5$) C, H, N; calcd. (%): 76.37, 5.07, 18.55; found (%): 76.39, 5.16, 18.60.

7-[(2-Chloroethoxy)methyl]adenine 12. To a solution of 11 (1.79 g, 4.74 mmol) in CH$_2$Cl$_2$ (70 mL) was added (2-chloroethoxy)methyl chloride (0.65 g, 5.0 mmol). The reaction mixture was stirred at 25° C. for 8.0 h to afford a solid. Filteration and crystallization from MeOH gave 12 (1.66 g, 4.27 mmol) in 90% yield: mp 184–186° C.; R$_f$ (hexanes/EtOAc=1:2) 0.28; UV (EtOH) $\lambda_{max}$ 267 ($\epsilon$ 14,600); $^1$H NMR (DMSO-d$_6$) $\delta$ 3.73 (t, J=4.5 Hz, 2 H, CH$_2$Cl), 3.86 (t, J=4.5 Hz, 2 H, OCH$_2$), 5.76 (s, 2 H, H$_2$C$_{1'}$), 8.49 (s, 1 H, HC$_2$), 8.74 (s, 1 H, HC$_8$), 9.32, 10.05 (2 br, 2 H, NH$_2$); $^{13}$C NMR (DMSO-d$_6$) $\delta$ 43.13 (CH$_2$Cl), 68.82 OCH$_2$ 78.10 (C$_{1'}$), 118.20 (C$_5$), 143.53 (C$_2$), 146.50 (C$_8$), 149.39 (C$_4$), 151.60 (C$_6$); MS m/z 227 (M$^+$, Cl-cluster). Anal. (C$_8$H$_{10}$ClN$_5$O) C, H, N, Cl; calcd (%): 42.20, 4.43, 30.76, 15.59; found (%): 42.32, 4.50, 30.69, 15.62.

7-[(2-(p-Methoxyphenyloxy)ethoxy)methyl]adenine 13. After 10 h, compound 13 (2.79 g, 8.86 mmol) was synthesized in 86% yield from 11 (3.90 g, 10.3 mmol) and (2-(p-methoxyphenyloxy)ethoxy)methyl chloride (2.25 g, 10.4 mmol) in CH$_2$Cl$_2$ (100 mL) by the method used for the synthesis of 12: mp 129–130° C.; R$_f$(hexanes/EtOAc=1:2) 0.21; UV (EtOH) $\lambda_{max}$ 270 ($\epsilon$ 15,100); $^1$H NMR (CD$_3$OD) $\delta$ 3.68 (s, 3 H, OCH$_3$), 4.04 (br s, 4 H, O(CH$_2$)$_2$O), 5.83 (s, 2 H, H$_2$C$_{1'}$), 6.58, 6.68 (AA'BB', J=9.0 Hz, 4 H, C$_6$H$_4$), 8.29 (s, 1 H, HC$_2$), 8.61 (s,1 H, HC$_8$); $^{13}$C NMR (CD$_3$OD) $\delta$ 56.03 (CH$_3$), 68.70 (OCH$_2$), 70.18 CH$_2$OPh 82.27 (C$_{1'}$), 119.59 (C$_5$), 144.17 (C$_2$), 147.57 (C$_8$), 150.25 (C$_4$), 151.97 (C$_6$), 115.50, 116.35, 153.44, 155.53 (C$_6$H$_4$); MS m/z 315 (M$^+$). Anal. (C$_{15}$H$_{17}$N$_5$O$_3$) C, H, N; calcd (%): 57.13, 5.43, 22.21; found (%): 57.24, 5.49, 22.34.

7-[(2-Hydroxyethoxy)methyl]adenine 14. Compound 14 (0.74 g, 3.54 mmol) was prepared in 80% yield from 13 (1.39 g, 4.43 mmol) and CAN (2.43 g, 4.43 mmol) in CH$_3$CN (30 mL) and water (10 mL) by the method used for the synthesis of 9: mp 122–123° C.; R$_f$(hexanes/EtOAc=1:2) 0.12; UV (EtOH) $\lambda_{max}$ 265 ($\epsilon$ 14,800); $^1$H NMR (CD$_3$OD) $\delta$ 3.69–3.79 (m, 4 H, O(CH$_2$)$_2$O), 5.79 (s, 2 H, H$_2$C$_{1'}$), 8.32 (s, 1 H, HC$_2$), 8.60 (s, 1 H, HC$_8$); $^{13}$C NMR (CD$_3$OD) $\delta$ 61.80 (CH$_2$OH), 72.27 (OCH$_2$) 82.01 (C$_{1'}$), 119.62 (C$_5$), 144.29 (C$_2$), 147.68 (C$_8$), 150.32 (C$_4$), 152.12 (C$_6$); MS m/z 209 (M$^+$). Anal (C$_8$H$_{11}$N$_5$O$_2$) C, H, N; calcd (%): 45.93, 5.30, 33.48; found (%): 45.80, 5.45, 33.51.

EXAMPLE 3

Synthesis of Compound 20

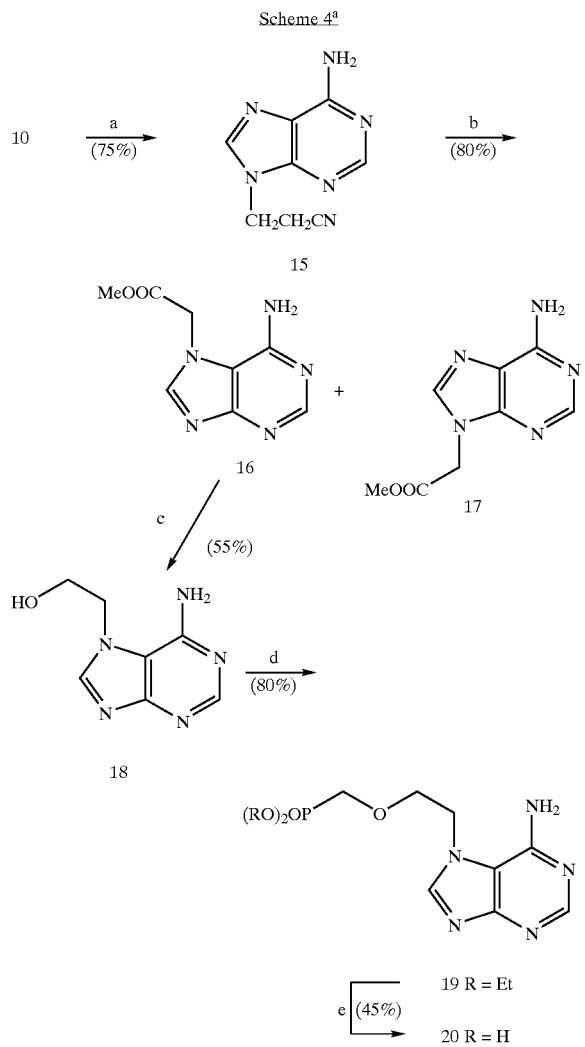

[a] Reagents and conditions: (a) BrCH$_2$CH$_2$CN, NaH, DMF, 65° C., 17.0 h. (b) ICH$_2$COOME, LiTMP, THF, -20 to -25° C., 16.0 h. (c) NaBH$_4$, wet THF, 25° C., 4.0 h. (d) Diethyl (p-toluenesulfonyloxymethane)phosphate, tert-butoxide, DMF, 25° C., 4.0 h. (e) Me$_3$SiBr, CH$_2$Cl$_2$/DMF, 25° C., 7.0 h.

As shown in Scheme 4, alkylation of adenine 10 with 3-bromopropionitrile in the presence of NaH in DMF gave N$^9$-(cyanoethyl)adenine 15 in 75% yield. Reaction of 15 with methyl iodoacetate and lithium 2,2,6,6-tetramethylpiperidine (Li TMP) in THF afforded a mixture of N$^7$-alkylated product 16 (60% yield) and N$^9$-isomer 17 (20% yield). Reduction of the ester group in 16 with NaBH$_4$ in wet THF[13] gave N$^7$-(hydroxyethyl)adenine 18 in 55% yield. Conversion of 18 to phosphonate 19 (60% yield) was accomplished by use of diethyl (p-toluenesulfonyloxymethane)phosphonate and sodium tert-butoxide in DMF.[14] Treatment of compound 19 with Me$_3$SiBr[15] then afforded phosphonic acid 20 in 45% yield.

9-(2-Cyanoethyl)adenine 15. To a suspension of 57% NaH in mineral oil (0.962 g, 22.8 mmol) in dry DMF (100 mL) was added 10 (3.40 g, 24.9 mmol) under nitrogen and the mixture was heated at 80° C. for 1.0 h. A solution of 3-bromopropionitrile (2.81 g, 21.0 mmol) in DMF (5.0 mL) was added at 25° C. and the reaction was heated at 65° C. for 17 h. It was then diluted with EtOAc (250 mL) and 5% aqueous HCl solution (150 mL). The organic layer was separated and then washed with water (4×100 mL). It was dried over MgSO$_4$ (s) and concentrated under reduced pressure. Purification of the residue was carried out by use of column chromatography (EtOAc/hexanes=7.5:2.5) to afford compound 15 (3.510 g, 18.67 mmol) in 75% yield: mp 148–150° C.; R$_f$(hexanes/EtOAc=1:2) 0.38; UV (EtOH) $\lambda_{max}$ 260 ($\epsilon$ 13,900); $^1$H NMR (CD$_3$OD) $\delta$ 2.92 (t J=5.8 Hz, 2 H, CH$_2$CN),3.43 (t, J=5.8 Hz, 2 H, CH$_2$N), 8.35 (s, 1 H, HC$_2$), 8.69 (s, 1 H, HC$_8$); MS m/z 188 (M$^+$).

7-[(Methoxycarbonyl)methyl]adenine 16 and 9-[(Methoxycarbonyl)methyl]-adenine 17. To a stirred solution containing 15 (0.134 g, 1.00 mmol) and methyl iodoacetate (0.30 g, 1.5 mmol) in dry THF (20 mL) was added a THF solution of LiTMP (2.8 mL, 1.2 mmol) dropwise under an argon atmosphere at −20° C. The reaction mixture was warmed to 25° C. within 1.0 h; then it was stirred at room temperature for 15 h. The solution was partitioned between EtOAc (40 mL) and water (40 mL). The organic layer was dried over MgSO$_4$ (s) and concentrated under reduced pressure. Purification of the residue by use of column chromatography (EtOAc/hexanes=8:2) gave compound 17 (0.041 g, 0.20 mmol) in 20% yield. Further elution of the column with EtOAc/hexanes (9:1) afforded 16 (0.123 g, 0.594 mmol) in 60% yield.

For 16: mp 112–114° C.; R$_f$(hexanes/EtOAc=1:2) 0.16; UV (EtOH) $\lambda_{max}$ 267 ($\epsilon$ 14,000); $^1$H NMR (CD$_3$OD) $\delta$ 3.83 (s 3H, CH$_3$), 4.37 (s, 2 H, H$_2$C$_{1'}$), 8.41 (s, 1 H, HC$_2$), 8.75 (s, 1 H, HC$_8$); MS m/z 207 (M$^+$). Anal (C$_8$H$_9$N$_5$O$_2$) C, H, N; calcd (%): 46.37, 4.38 33.80; found (%): 46.32, 4.35, 33.83.

For 17: mp 148–149° C.; R$_f$(hexanes/EtOAc=1:2) 0.29; UV (EtOH) $\lambda_{max}$ 260 ($\epsilon$ 13,750); $^1$H NMR (CD$_3$OD) $\delta$ 3.75 (s, 3H, CH$_3$), 4.15 (s, 2 H, H$_2$C$_{1'}$), 8.29 (s, 1 H, HC$_2$), 8.38 (s, 1 H, HC$_8$); MS m/z 207 (M$^+$).

7-(2-Hydroxyethyl)adenine 18. To a stirred solution containing 16 (0.207 g, 0.999 mmol) and water (0.50 mL) in THF (12 mL) was added NaBH$_4$ (0.38 g, 10.0 mmol). After stirring for 4 h at 25° C., the reaction mixture was neutralized to pH=7.0 by use of 10% HCl aqueous solution. Solvent was evaporated under reduced pressure and the residue was purified by column chromatography (EtOAc/hexanes=9:1) to give 18 (0.10 g, 0.55 mmol) in 55% yield: mp 132–133° C.; R$_f$(hexanes/EtOAc=1:2) 0.09; UV (EtOH) $\lambda_{max}$ 265 ($\epsilon$ 14,110); $^1$H NMR (CD$_3$OD) $\delta$ 3.68 (t, J=5.9 Hz, 2 H, CH$_2$O), 3.66 (t, J=5.9 Hz, 2 H, CH$_2$N), 8.34 (s, 1 H, HC$_2$), 8.68 (s, 1 H, HC$_8$); MS m/z 179 (M$^+$). Anal (C$_7$H$_9$N$_5$O) C, H, N; calcd (%): 46.92, 5.06, 39.08; found (%): 47.01, 5.12, 39.11.

7-[2-(D)iethylphosphonomethoxy)ethyl]adenine 19. To a solution of 18 (0.18 g, 0.10 nmmol) in DMF (15 mL) was added sodium tert-butoxide (0.150 g, 1.56 mmol). After 5 min, diethyl (p-toluenesulfonyloxymethane)phosphonate (0.42 g, 1.3 mmol) was added and the reaction mixture stirred at 35° C. for 4.0 h. The reaction was then quenched with acetic acid (5.0 mL) and the mixture was partitioned between EtOAc (50 mL) and water (50 mL). The organic layer was separated and then washed with water (5×60 mL), dried over MgSO$_4$ (s), filtered, and concentrated under reduced pressure. Purification by use of column chromatography (EtOAc/MeOH=9:1) gave 19 (0.20 g, 0.60 mmol) in 60% yield as a white foam: R$_f$(hexanes/EtOAc=1:2) 0.16; UV (EtOH) $\lambda_{max}$ 266 ($\epsilon$ 15,321); $^1$H NMR (CD$_3$OD) $\delta$ 1.39 (t, J=6.7 Hz, 6H, 2 CH$_3$), 3.74 (t, J=6.3 Hz, 2 H, CH$_2$N), 3.76 (d, J=9.0 Hz, 2 H, CH$_2$P), 3.97–4.29 (m, 6 H, CH$_2$O+2

CH$_2$OP), 8.37 (s, 1 H, HC$_2$), 8.77 (s, 1 H, HC$_8$); MS m/z 329 (M$^+$). Anal (C$_{12}$H$_{20}$N$_5$O$_4$P) C, H, N; calcd (%): 43.76, 6.12, 21.27; found (%): 43.87, 6.21, 21.36.

7-[2-(Phosphonomethoxy)ethyl]adenine 20 To a solution of 19 (3.29 g, 10.0 mmol) in CH$_2$Cl$_2$ (130 mL) and DMF (10 mL) was added Me$_3$SiBr (4.95 g, 30.0 mmol); then the solution was stirred at 25° C. for 7.0 h. A mixture of MeOH and water (5:1, 40 mL) was added, and solvents were evaporated. Purification by use of column chromatography (EtOAc/MeOH=6:4) afforded 20 (1.23 g, 4.50 mmol) in 45% yield: mp 253° C. (dec.); R$_f$ (hexanes/EtOAc=1:2) 0.05; UV (EtOH) λ$_{max}$ 265 (ε 14,700); $^1$H NMR (CD$_3$OD) δ 3.66 (t, J=6.4 Hz, 2 H, CH$_2$N), 3.71 (d, J=8.7 Hz, 2 H, CH$_2$P), 4.19 (t, J=6.4 Hz, 2 H, CH$_2$O), 8.36 (s, 1 H, HC$_2$), 8.78 (s, 1 H, HC$_8$); MS m/z 273 (M$^+$). Anal (C$_8$H$_{12}$N$_5$O$_4$P) C, H, N; calcd (%): 35.17, 4.43, 25.63; found (%): 35.21, 4.41, 25.71.

EXAMPLES 4–7

Synthesis of Compound 24, 25, 28, and 29

Scheme 5$^a$

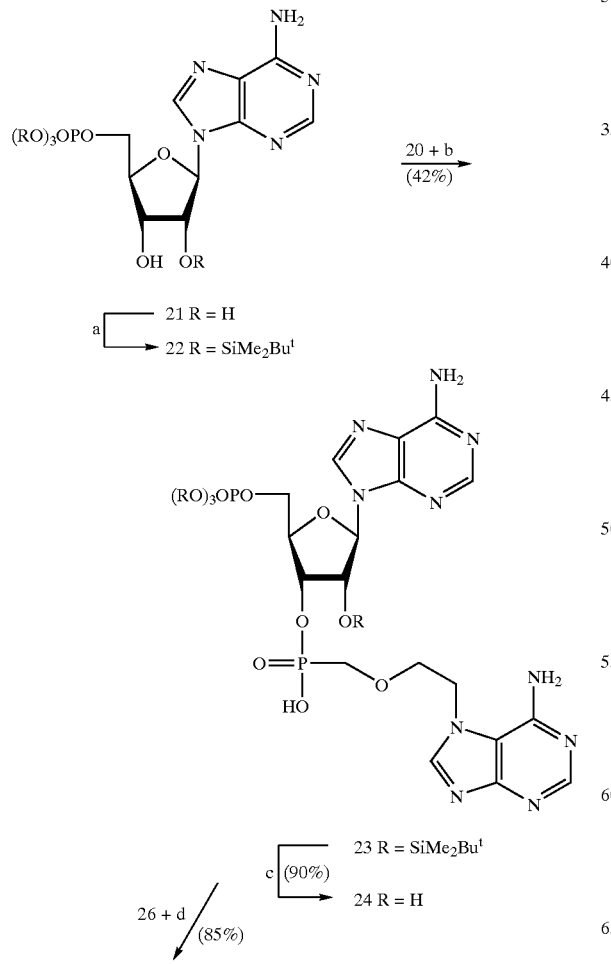

21 R = H
a
22 R = SiMe$_2$Bu$^t$

23 R = SiMe$_2$Bu$^t$
c (90%)
24 R = H

26 + d (85%)

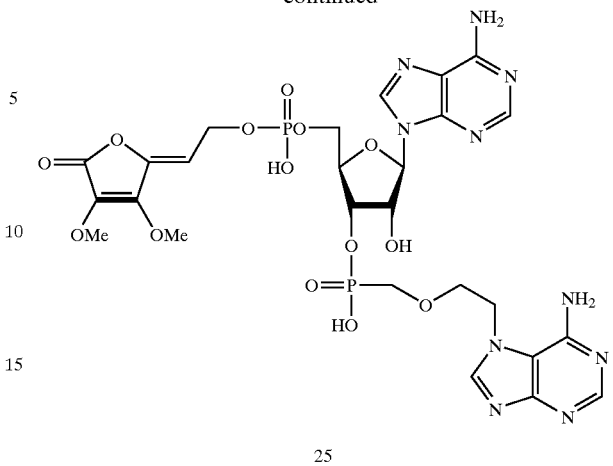

25

$^a$ Reagents and conditions: (a) Bu$^t$Me$_2$SiCl, AgNO$_3$, pyridine/CH$_3$CN, 25° C., 7.0 h. (b) CCl$_3$SO$_2$Cl, collidine, THF, 25° C., 10.0 h. (c) n-Bu$_4$NF, THF, 25° C., 30 min. (d) NaHCO$_3$, DMF, 25° C., 1.0 h.

Scheme 6

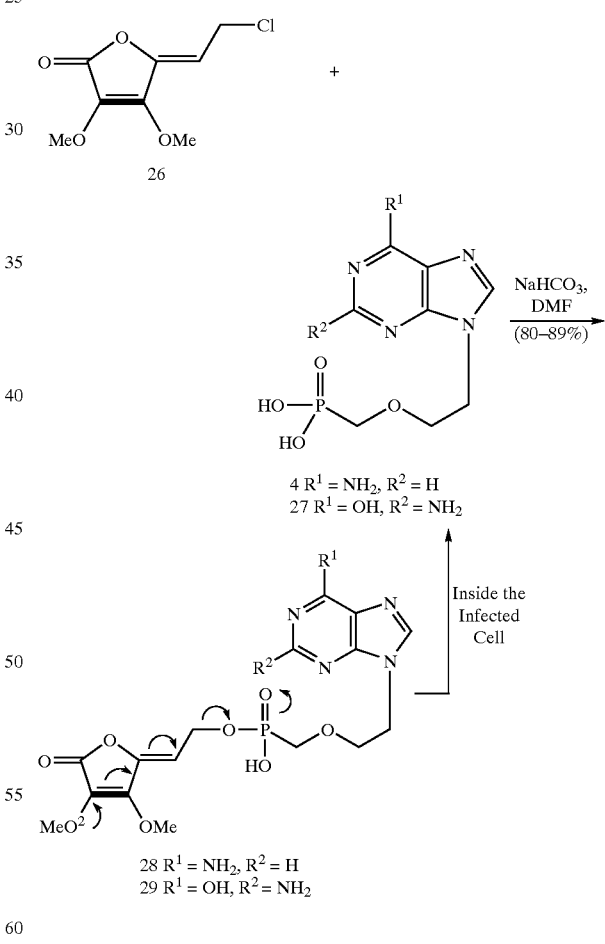

4 R$^1$ = NH$_2$, R$^2$ = H
27 R$^1$ = OH, R$^2$ = NH$_2$

Inside the Infected Cell

28 R$^1$ = NH$_2$, R$^2$ = H
29 R$^1$ = OH, R$^2$ = NH$_2$

As shown in Schemes 5 and 6, the nucleotide analog 24 was readily obtained in three steps from adenosine 5'-monophosphate 21, starting with silylation of phosphate 21 in CH$_3$CN with t-BuMe$_2$SiCl in the presence of AgNO$_3$ and pyridine. See, e.g., Ogilvie et al. (1983) Can. J. Chem. 61: 1204–1212. The resulting trisilylated compound 22 was condensed with phosphonic acid 20 using trichloromethanesulfonyl chloride in collidine and THF to afford dinucleotide 5'-monophosphate 23 in 42% overall yield. See, e.g., Hakimelahi et al. (1995) *J. Med. Chem.* 38: 4648–4659 and references cited therein. Desilylation of 23 with n-Bu$_4$NF in THF at 25° C. gave dinucleotide 24 in 90% yield which was then reacted with (Z)-4-(2-chloroethylidene)-2,3-dimethoxy-$\Delta^{a,b}$-butenolide (26) in the presence of NaHCO$_3$ in DMF to afford the target molecule 25 in 85% yield (Hakimelahi et al. (2001) *J. Med. Chem.* 44: 1749–1757). Similarly, treatment of compound 26 with either 9-[2-(phosphonomethoxy)ethyl]adenine (PMEA 4) or 9-[2-(phosphonomethoxy)ethyl]guanine (PMEG 27) in the presence of NaHCO$_3$ in DMF respectively gave an 80% or 88% yield of the desired compound 28 or 29.

9-[2'-O-(tert-butyldimethylsilyl)-5'-O-(phosphono)-β-D-furanosyl]adenine-3'-[[1-(adenin-7-yl-ethoxy)methyl]phosphonate] 23. To a solution of adenosine 5'-monophosphate (21) monohydrate (3.65 g, 9.99 mmol) in a mixture of pyridine (150 mL) and CH$_3$CN (160 mL) was added AgNO$_3$ (6.63 g, 39.0 mmol). After 10 min, tert-butyldimethylsilyl chloride (5.70 g, 37.8 mmol) was added. The mixture was stirred at 25° C. for 7.0 h and then filtered to remove AgCl. The filtrate was evaporated and the resultant crude product 22 was dissolved in dry THF (40 mL). In another flask, collidine (3.66 g, 30.0 mmol) was added to a solution of THF (45 mL) containing 20 (2.73 g, 10.0 mmol) at −10° C. To this solution was added CCl$_3$SO$_2$Cl (2.20 g, 10.0 mmol) in THF (15 mL) dropwise. After crude 22 in THF was added to the mixture, it was stirred at 25° C. for 10 h. The solvents were removed, and the residue was dissolved in AcOEt (100 mL) and washed with water (3×100 mL). The organic layer was concentrated, and the residue was purified by use of column chromatography (EtOAc/MeOH=6:4) to afford 23 (3.0 g, 4.2 mmol) in 42% overall yield: mp 223–225° C.; UV (EtOH) $\lambda_{max}$ 264 (ε 17,300); $^1$H NMR (CD$_3$OD) δ 0.16 (brs, 6 H, (CH$_3$)$_2$Si), 1.05 (s, 9 H, (CH$_3$)$_3$C), 3.67–4.27 (m, 8 H, CH$_2$N+CH$_2$O+CH$_2$OP+CH$_2$P), 4.32–4.5 (m, 3H, HC$_2$'+HC$_3$'+HC$_4$'), 6.58 (d, J=4.9 Hz, 1 H, HC$_1$'), 8.12, 8.42 (2s, 2 H, 2×HC$_2$), 8.27, 8.89 (2s, 2 H, 2×HC$_8$). Anal (C$_{24}$H$_{38}$N$_{10}$P$_2$Si) C, H, N; calcd (%) 40.22, 5.34, 15.94; found (%): 40.29, 5.38, 19.50.

9-[5'-O-(phosphono)-β-D-furanosyl]adenine-3'-[[1-(adenin-7-yl-ethoxy)methyl]phosphonate] 24. To a solution of 23 (0.36 g, 0.50 mmol) in THF (5.0 mL) was added n-Bu$_4$NF (1.0 M solution in THF, 0.31 g, 1.2 mmol). Acetic acid (0.50 mL) was added to the mixture after it was stirred at 25° C. for 30 min. The solvents were removed, and the residue was purified by use of Whatman 3-mm paper with a mixture of i-PrOH, NH$_4$OH, and H$_2$O (9:1:2) as the eluent. The band at ca. R$_f$ 0.35 was eluted with H$_2$O and collected by lyophilization to give 24 (0.27 g, 0.45 mmol) in 90% yield: mp>250° C. dec; UV (EtOH) $\lambda_{max}$ 264 (ε 18,200); $^1$H NMR (CD$_3$OD) δ 3.75–4.18 (m, 8 H, CH$_2$N+CH$_2$O+CH$_2$OP+CH$_2$P), 4.29–4.70 (m, 3H, HC$_2$'+HC$_3$'+HC$_4$'), 6.48 (d, J=4.5 Hz, 1 H, HC$_1$'), 7.99, 8.39 (2s, 2 H, 2×HC$_2$), 8.26, 8.83 (2s, 2 H, 2×HC$_8$). Anal (C$_{18}$H$_{24}$N$_{10}$O$_{10}$P$_2$) C, H, N; calcd (%): 35.88, 4.02, 23.25; found (%): 35.82, 4.12, 23.17.

9-[[(Z)-4-(ethylidene)-2,3-dimethoxy-$\Delta^{a,b}$-butenolide]-β-D-furanosyl]adenine-3'-[[1-(adenin-7-yl-ethoxy)methyl]phosphonate]-4,5'-phosphate 25. To a solution of 24 (0.300 g, 0.499 mmol) in DMF (20 mL) was added NaHCO$_3$ (0.30 g, 3.6 mmol). The reaction mixture was stirred at 25° C. under N$_2$ for 10 min. Then, butenolide 26 (0.10 g, 0.50 mmol) was added and stirred under N$_2$ for 1.0 h. The solution was diluted with EtOAc (50 mL) and aqueous HCl solution (1%, 40 mL). The organic layer was separated and washed with H$_2$O (50 mL). Then, it was dried over MgSO$_4$ (s), filtered, and concentrated under reduced pressure. Purification by use of silica gel column chromatography with EtOAc/MeOH (6:4) as eluant afforded 25 (0.32 g, 0.42 mmol) in 85% yield: mp>237° C. dec; UV (EtOHl) $\lambda_{max}$ 215 (ε 16,000), $\lambda_{max}$ 264 (ε 18,540); $^1$H NMR (CD$_3$OD) δ 3.69–4.12 (m, 16 H, CH$_2$N+CH$_2$O+2×CH$_2$OP+CH$_2$P+ C$_2$OCH$_3$+C$_3$OCH$_3$), 4.31–4.78 (m, 3H, HC$_2$'+HC$_3$'+HC$_4$'), 5.38 (t, J=7.0 Hz, 1 H, =CH), 6.51 (d, J=4.8 Hz, 1 H, HC$_1$'), 8.02, 8.40 (2s, 2 H. 2×HC$_2$), 8.28, 8.86 (2s, 2 H, 2×HC$_8$). Anal (C$_{26}$H$_{32}$N$_{10}$O$_{14}$P$_2$) C, H, N; calcd (%): 40.52, 4.19, 18.18; found (%): 40.61, 4.22, 18.21.

[1-(Adenin-9-yl-ethoxy)methyl]phosphono-6-yl-(Z)-4-(ethylidene)-2,3-dimethoxy-$\Delta^{a,b}$-butenolide 28. Compound 28 (3.90 g, 8.80 mmol) was prepared in 88% yield from 4 (2.73 g, 9.99 mmol) and 26 (2.20 g, 10.0 mmol) in the same manner that 25 was prepared from 24: mp>241° C. (dec.); R$_f$(hexanes/EtOAc=1:2) 0.12; UV (EtOH) $\lambda_{max}$ 218 (ε 13,097), $\lambda_{max}$ 259 (ε 14,700); $^1$H NMR (CD$_3$OD) δ 3.57 (t, J=6.0 Hz, 2 H, CH$_2$N), 3.69 (d, J=9.0 Hz, 2 H, CH$_2$P), 3.89 (m, 5 H, C$_2$OCH$_3$+CH$_2$OP), 4.06, (t, J=6.0 Hz, 2 H, CH$_2$O), 4.13 (s, 3 H, C$_3$OCH$_3$), 5.41 (t, J=7.0 Hz, 1H, =CH), 8.12 (s, 1 H, HC$_2$), 8.21 (s, 1 H, HC$_8$); MS m/z 441 (M$^+$). Anal (C$_{16}$H$_{20}$N$_5$O$_8$P) C, H, N; calcd (%): 43.54, 4.57, 15.86; found (%): 43.66, 4.46, 15.95.

[1-(Guanine-9-yl-ethoxy)methyl]phosphono-6-yl-(Z)-4-(ethylidene)-2,3-dimethoxy-$\Delta^{a,b}$-butenolide 29. Compound 29 (3.7 g, 8.0 mmol) was prepared in 80% yield from 27 (2.89 g, 9.99 mmol) and 26 (2.20 g, 10.0 mmol) in the same manner that 25 was prepared from 24: mp>260° C. (dec.); R$_f$(hexanes/EtOAc=1:2) 0.05; UV (EtOH) $\lambda_{max}$ 252 (ε 11,097), $\lambda_{max}$ 273 (ε 8,100); $^1$H NMR (CD$_3$OD) δ 3.71 (t, J=7.2 Hz, 2 H, CH$_2$N), 3.79 (d, J=9.1 Hz, 2 H, CH$_2$P), 3.92 (m, 5 H, C$_2$OCH$_3$+CH$_2$OP ), 4.10, (t, J=7.2 Hz, 2 H, CH$_2$O), 4.18 (s, 3 H, C$_3$OCH$_3$), 5.50 (t, J=6.8 Hz, 1H, =CH), 8.76 (s, 1 H, HC$_8$); MS m/z 457 (M$^+$). Anal. (C$_{16}$H$_{20}$N$_5$O$_9$P) C, H, N; calcd (%): 42.02, 4.41, 15.31; found (%): 42.14, 4.50, 15.25.

EXAMPLE 8

Enzyme Assays

For comparison, compounds 1, 9-[(2-hydroxy-ethoxy)methyl]guanine (acyclovir 2), 9-(β-D-arabinofaranosyl)adenine (ara-A 3), 9-[2-(phosphonomethoxy)ethyl]adenine (PMEA, 4), and 9-[2-(phosphonomethoxy)ethyl]guanine (PMEG 27) were either synthesized or purchased from a commercial source.

9-[(2-Hydroxyethoxy)methyl]adenine 1. Compound 1 was prepared by an standard procedure: see Davari (1989) Doctoral Thesis, School of Veterinary Medicine, Shiraz University, Shiraz, Iran. Mp 198–199° C.; R$_f$(hexanes/EtOAc=1:2) 0.23; UV (EtOH) $\lambda_{max}$ 259 (ε 14,000); $^1$H NMR (CD$_3$OD) δ 3.62 (s, 4 H, O(CH$_2$)$_2$O), 5.67 (s, 2 H, H$_2$C$_1$'), 8.22 (s, 1 H, HC$_2$), 8.27 (s, 1 H, HC$_8$); $^{13}$C NMR (CD$_3$OD) δ 61.86 (CH$_2$OH), 72.08 (OCH$_2$) 74.31 (C$_1$'), 119.98 (C$_5$), 143.14 (C$_8$), 150.90 (C$_4$), 153.74 (C$_2$), 157.19 (C$_6$); MS m/z 209 (M$^+$).

Lipophilicity and Solubility Tests. Lipophilicity and water solubility were determined by the distribution between 1-octanol and water according to the methods reported by Baker et al. (1978, *J. Med. Chem.* 21: 1218–1221). The results show in Table 1.

To determine lipohoilicity (Partition Coefficients), a solution of each compound (10 mL) in phosphate buffer (0.10 M) possessing an UV absorbance of 2.2–3.3 at 258–267 nm, for adenine, or at 270–290 nm, for guanine, was shaken with 1-octanol (10 mL) in a separatory funnel for 1.5 h. The layers were separated and their concentrations were determined by an UV spectrophotometer. The partition coefficient was calculated as $P=[S]_{1-octanol}/[S]_{H_2O}$. To determine solubility, each compound (70 mg) was agitated in a 25-mL volumetric flask with phosphate buffer (0.10 M, pH 6.8, 5.0 mL) for 20 h. This solution was filtered from undissolved solid through a sintered glass funnel (4.0–5.5 mesh ASTM) and the concentration of the solution was determined by UV absorbance.

The results show that adenine acyclic nucleosides 1 and 14 were observed to exhibit higher lipophilicity as well as water solubility than those exhibited by $N^7$-guanine acyclic nucleoside 9, acyclovir 2, and ara-A 3. Phosphonate 20 and butenolide ester derivatives 25, 28, and 29 also exhibited higher lipophilicity and water solubility as compared to PMEA 4 or PMEG 27. On the other hand, even though the solubility of nucleotide analog 24 in water was found to be higher than that of PMEA 4, its lipophilicity was lower than that of 4. Furthermore, butenolide ester derivative 25 showed higher lipophilicity as well as water solubility with respect to the parent nucleotide 5'-monophosphate 24.

Kinetic Studies of Competitive Inhibition of Adenosine Deaminase by Acyclic Nucleosides and Nucleotides. The rates of deamination of $N^9$-alkylated adenine 1, ara-A, 3, PMEA 4, $N^7$-alkylated adenine 14, phosphonate 20, dinucleotide 5'-monophosphate 24, its butenolide ester derivative 25, and PMEA-containing butenolide 28 in the presence of calf mucosal adenosine deaminase (ADA, EC 3.5.4.4) in buffer solutions were determined. See, e.g., Ogilvie et al. (1984) Can. J. Chem. 62: 241–252 and references cited therein. Additionally, the inhibition studies on these compounds were carried out based on the Kaplan method (Table 2). See, e.g., Moosavi-Movahedi et al. (1993) Int. J. Biol. Macromol. 15: 125–129 and references cited therein. The results (Table 2) showed that both the $N^9$- and $N^7$-acyclic nucleosides 1 and 14 functioned as ADA substrates. The $V_{max}$ of 14 was less than that of 1 by a factor of 4. Compounds 1, 14, and 24 showed competitive inhibition of ADA when ara-A was used as a substrate. However, $N^7$-isomer 14 was found to be more efficient than the $N^9$-isomer 1 and nucleotide analog 24 as an inhibitor of ADA. PMEA 4, acyclic nucleoside phosphonate 20, and nucleotide-containing butenolides 25 and 28 were neither a good substrate nor an inhibitor of the enzyme. Nucleotide analog 24, however, was a substrate for ADA, but its $V_{max}$ was about 95% less than that of ara-A 3. The slow rate of deamination of compound 24 by ADA may reflect the lack of substrate activity of the acyclic nucleoside phosphonate moiety therein in the active site of the enzyme.

Comparison of Phosphorylation of Nucleosides by HSV and Vero Cell Thymidine Kinases. Phosphorylation of nucleosides with HSV or Vero cell thymidine kinase was studied as described previously. See, e.g., Keller et al. (1981) Biochem. Pharmacol. 30: 3071–3077 and references cited therein. Results are summarized in Table 3. The rate of phosphorylation of $N^9$-adenine acyclic nucleoside 1, acyclovir 2, ara-A 3, $N^7$-guanine acyclic nucleoside 9, and $N^7$-adenine acyclic nucleoside 14 as well as a mixture of 2 and 14 (w/w=1:1), a mixture of 1 and 2 (w/w=1: 1), and a mixture of 2 and 3 (w/w=1:1) in the presence of HSV or Vero cell thymidine kinase was determined and the results were compared with those of thymidine. It was observed that $N^7$-guanine nucleoside 9, unlike acyclovir, can be phosphorylated by both the HSV thymidine kinase and the host cell kinase. On the other hand, these enzymes were found not to phosphorylate adenine nucleosides 1, 14, and ara-A 3; yet the $N^7$-adenine nucleoside 14 induced a 2-fold increase on the rate of phosphorylation of acyclovir 2 (see Table 3). $N^9$-adenine nucleosides 1 and 3, however, did not induce any increase on the rate of phosphorylation of 2. It is believed that the $N^7$-adenine nucleoside 14 binds (Km=30 mM) to a specific receptor at the active site of the enzyme to exhibit the observed activatory property toward the HSV thymidine kinase.

Enzymatic Conversion of Acyclic Nucleoside Phosphonates and Nucleotide 5'-Monophosphate Analog to Their Antivirally Active Diphosphates (Triphosphate Equivalents). Substrate affinities of acyclic nucleoside phosphonates 4, 20, 21, and dinucleotide analog 24 for PRPP synthetase as well as their inhibitory effect against the enzyme were evaluated according to the established procedures. See, e.g., Balzarini et al. (1991) J. Biol. Chem. 266: 8686–8689 and references cited therein. Results are illustrated in Table 4. The assays were then terminated after 4 h by the addition of MeOH. HPLC on an anion-exchange Partisphere column was used to analyze the formation of ATP 21pp, PMEApp, 4pp, 20pp, and 24pp.

The substrate affinity of $N^7$-acyclic nucleoside phosphonate 20 (Km=4.8 mM) for the enzyme was found to be 4-times less than that of PMEA 4 (Km=1.5 mM). Similarly, the $V_{max}$ for conversion of 20 to 20pp is at least 7-times lower than that for the conversion of 4 to 4pp. On the other hand, nucleotide analog 24 was found to be a better substrate than PMEA 4 for PRPP synthetase (Km=0.57 mM). It can also be phosphorylated ($V_{max}$=12) by the enzyme at a rate similar to that of AMP 21 ($V_{max}$=14).

It has been hypothesized (Balzarini supra) that the primary amino group at the C-6 position of purines is essential for hydrogen bonding with the enzyme. The $NH_2$ group in 20 is sterically hindered by an adjacent side chain at the N-7 position. As such, it cannot as effectively interact with the active site of the enzyme when compared to PMEA 4, natural substrate AMP 21, or nucleotide analog 24.

Activity of Snake Venom and Spleen Phosphodiesterases Against Nucleotide Analogs. Snake venom phosphodiesterase (200 units) was dissolved in tris(hydroxymethyl) aminomethane buffer (1.0 mL), which was adjusted to pH 9.2 with 0.1 N HCl. The enzyme solution (0.10 mL) was added to the nucleotide 24 or 25 (0.70 mg) and the mixture was incubated at 37° C. for 8 h. The solution was then applied to Whatman 3-mm paper as a band, which was developed with a mixture of i-PrOH, conc. $NH_4OH$, and $H_2O$ (9:1:2). Degradation products or unreacted starting materials were separated. Dinucleotide 5'- monophosphate 24 gave 9-(β-D-furanosyl)adenine-3'-[[1-(adenin-7-yl-ethoxy)methyl]phosphonate] in about 80% yield. On the other hand, dinucleotide-containing butenolide 25 was completely resistant to the enzyme.

Spleen phosphodiesterase (20 units) was dissolved in sodium pyrophosphate buffer (0.01 M, 1.0 mL), which was adjusted to pH 6.5 with phosphoric acid. Nucleotide 24, 25, or 9-(β-D-furanosyl)adenine-3'-[[1-(adenin-7-yl-ethoxy)methyl]phosphonate] (0.70 mg) was dissolved in ammonium acetate buffer (0.05 M, 0.20 mL), which was adjusted to pH 6.5 with acetic acid. An aliquot of the enzyme solution (0.1 mL) was added to the nucleotide solution and the mixture was incubated at 37° C. for 8 h. The solution was then applied to Whatman 3-mm paper as a band and developed with a mixture of i-PrOH, conc. $NH_4OH$, and $H_2O$ (9:1:2). Bands containing products were cut out, which were eluted with $H_2O$ and the resultant mixture was freeze-dried. The isolated products were characterized by comparison with authentic samples.

Dinucleotide 24 afforded phosphonate 20 and adenosine 5'-monophosphate 21 in about 60% yield. 9-(β-D-Furanosyl)adenine-3'-[[1-(adenin-7-yl-ethoxy)methyl]-phosphonate] gave adenosine (40% yield) and 20 (60% yield). Dinucleotide analog 25, having a butenolide ester unit, was found to be stable to the enzyme. Compound 24, possessing both the skeletons of phosphonate 20 and 5'-adenosine monophosphate 21, was dephosphorylated at the 5'-position by snake venom in 80% yield after 8 h. The resultant 9-(b-D-furanosyl)adenine-3'-[[1-(adenin-7-yl-ethoxy)methyl]phosphonate] was hydrolyzed further in the presence of spleen phosphodiesterase to afford adenosine and phosphonate 20 in about 40–60% yield after 8 h. See, Hakimelahi et al. (1995) *J. Med. Chem.* 38: 4648–4659 and references cited therein. Spleen phosphodiesterase also degraded compound 24 to give 5'-adenosine monophosphate 21 and phosphonate 20 in an overall yield of 60% after 8 h. These results indicate that the phosphodiesterases recognized dinucleotide analog 24 as a normal substrate. In addition, it was found that nucleotide-containing butenolide 25 was completely resistant to snake venom and spleen enzymes.

EXAMPLE 9

In Vitro Assays

Anti-DNA Virus Activity in Vitro. The newly synthesized compounds were tested for inhibition of cytopathogenicity of the herpes simplex type 1 virus (HSV-1), herpes simplex type 2 virus (HSV-2), thymidine kinase-positive (TK$^+$) and thymidine kinase-deficient (TK$^-$) strains of varicella-zoster virus (VZV), and human cytomegalovirus in Vero cell culture up to a level as high as 128 mg/mL. Compounds tested include N$^7$-alkylated purines 7, 9, 12, 14, 20, as well as a mixture of 1 and 14 (w/w=1:1), 2 and 14 (w/w=1:1), 3 and 14 (w/w=1:1) in addition to N$^9$-substituted adenine 1, acyclovir 2, ara-A 3, PMEA 4, PMEG 27, nucleotide analog 24, and nucleotide-containing butenolides 25, 28, and 29. Toxicity of these compounds was evaluated by their ability to cause morphological changes in HeLa and Vero cells at different concentrations. The minimum inhibitory concentrations (IC$_{50}$) were measured by use of the linear regression method. See, e.g., Armitage (1983) "Statistical Methods in Medical Research," Blackwell Scientific Publications, Oxford, U.K.; and Hakimelahi et al. (1990) *J. Sci. Iran* 1: 186–191. The results are summarized in Table 5.

The pronounced anti-DNA virus activity of 14 with respect to the corresponding chloro derivative 12 showed that the presence of a hydroxyl group is essential for antiviral activity. Results from the biological tests also indicated that adenine nucleoside 14 was not effectively deaminated by ADA; yet it inhibited the deactivating property of the enzyme and led to the observed increase in the antiviral activity of 1 and ara-A 3. Furthermore, use of adenine acyclic nucleoside 14 resulted in a 2-fold increment in the rate of phosphorylation of acyclovir 2 by HSV-thymidine kinase. As such, a combination of 14 and 2 exhibited profound antiviral activity. N$^7$-Adenine nucleoside 14 was found to be less toxic than the corresponding N$^9$-isomer 1. On the other hand, both HSV and cellular thymidine kinases can phosphorylate N$^7$-guanine nucleoside 9. As a result, this nucleoside exhibited more toxicity than acyclovir 2.

The rate of phosphorylation of N$^7$-acyclic nucleoside phosphonate 20 to its antivirally active anabolite 20pp by PRPP synthetase is 7-times less than that of the PMEA 4. Thus in comparison to compound 4, compound 20 exhibited less activity against DNA-viruses. On the other hand, nucleotide 5'-monophosphate analog 24, possessing a natural AMP moiety, was converted to its diphosphate (triphosphate form) 24pp at a rate comparable to that of AMP 21, which is about 120-times faster than the rate of conversion of PMEA 4 to PMEApp 4pp. Consequently, nucleotide 5'-monophosphate 24 exhibited higher anti-DNA virus activity than PMEA 4.

The ability of a drug to penetrate a membrane and exhibit biological activity can be correlated to its lipophilicity. See, e.g., Hakimelahi et al. (1995). *J. Med. Chem.* 38: 4648–4659 and references cited therein. Consequently, compounds 25, 28, and 29 possessed butenolide ester functionalities as lipophilic prodrugs. These compounds displayed superior antiviral activity relative to their respective parent compounds nucleotide 5'-monophosphate 24, PMEA 4, and PMEG 27. In addition, spleen phosphodiesterase can recognize and at least partly hydrolyze nucleotide analog 24 to the biologically less active phosphonate 20 inside the infected cells; whereas its butenolide ester derivative 25 was found to be stable toward phosphodiesterases. Thus in comparison with nucleotide analog 24, its prodrug 25 possesses superior bioavailability and greater stability both in vitro and in vivo.

Anti-Retrovirus Activity in Vitro. The methods for measuring viruses-induced cytopathogenicity in MT4 cells or CEM cells, as well as the toxicity of the tested compounds towards MT4 and CEM cells have been described previously. See, e.g., Averett (1989) *J. Virol. Methods* 23: 263–276. Results are summarized in Table 6.

Compounds 4, 20, 24, 25, 27, 28, and 29 were tested for inhibition of cytopathogenicity against the human immunodeficiency viruses HIV-1 (III-B) and HIV-2 (LAV-2) in MT4 cells. These compounds were also screened for their antiviral activity against moloney murine sarcoma virus (MSV) in CEM cells in a cell-protection assay.[30] Toxicity of these compounds was evaluated by their ability to cause morphological changes in MT4 or CEM cells at different concentrations. The minimum inhibitory concentrations (IC$_{50}$) were measured by the use of the linear regression method (Table 6).

In comparison to the rate of phosphorylation of PMEA 4 to PMEApp 4pp by PRPP synthetase, the conversion of dinucleotide 24 to its anabolically active form 24pp is 120 times faster; yet PMEA 4 exhibited higher activity than 24 as well as the butenolide ester derivative 25 against retroviruses. Thus, the HIV and MSV reverse transcriptases may have higher affinity for PMEA 4 than dinucleotide analog 24. PMEA 4 was also found to be more active than its N$^7$-isomer 20 against retroviruses. On the other hand, butenolide ester derivatives 28 and 29 displayed superior antiviral activity relative to their respective parent molecules 4 and 27. Thus in comparison to PMEA 4 and PMEG 27, their respective lipophilic prodrugs 28 and 29 possess superior bioavailability and greater anti-retrovirus activity. As shown in Scheme 6, we believe that the oxygen of the methoxy group at the C-2 position of the butenolide moiety is responsible for the ease of conversion of these novel prodrugs 28 and 29 to their corresponding potential drugs PMEA 4 and PMEG 27 inside the infected cells.

EXAMPLE 10

In Vivo Assays

Anti-HSV-1 Activity in Vivo and Determination of LD$_{50}$ for N$^7$-Adenine Acyclic Nucleoside 14, Nucleotide- Containing Butenolide 25, and PMEA-Containing Butenolide 28 in Mice. Two-weeks-old NMRI mice (15–20 animals/group), weighing ca. 7 g each, were infected i.p. with 4×10⁴ units of HSV-1 (KOS). See, e.g., Kim et al. (1991) *J. Med. Chem.* 1991, 34, 2286–2294. Compounds in Table 7 were administered i.p. once a day for 6 consecutive days, starting 4 h postinfection. Percentage of HSV-1-infected mice without symptoms and those that were alive at day 21 postinfection were observed (see Table 7). Deaths were recorded for 21 days after infection.

Acyclovir 2, PMEA 4, N7-guanine acyclic nucleoside 9, $N^7$-adenine acyclic nucleoside 14, $N^7$-acyclic nucleoside phosphonate 20, nucleotide 5'-monophosphate 24, and butenolide ester derivatives 25 and 28 were evaluated for their inhibitory effect on HSV-1-induced mortality in $NMR_1$ mice (Table 6). Butenolide derivative of PMEA, 28, appeared to be the most potent anti-HSV-1 agent in vivo, followed by nucleotide-containing butenolide 25, nucleoside analog 14, nucleotide analog 24, acyclovir 2, PMEA 4, phosphonate 20, and nucleoside analog 9. Since compound 28 is less active in vitro against HSV-1 when compared to compounds 25 and 14 respectively, the in vitro potency does not directly translate to in vivo potency. These results confirmed previous findings. See, e.g., De Clercq et al. (1986) *Nature* (London) 323: 464–467; and Pauwels et al. (1988) *Agents Chemother*. 32: 1025–1030.

All compounds were administered intraperitoneally (i.p., 100–250 mg/kg/day) for 6 consecutive days. Compounds 2, 4, 14, 24, and 25 gave full protection against HSV-induced mortality at the 150 mg/kg dose level. The same level of protection was provided by compound 28 at a dose of 100 mg/kg. Survival times of all treated groups were found to be significantly different from the placebo treated control group (see Table 7). The potent anti-HSV-I activity exhibited by compounds 2, 4, 14, 24, 25, and 28 clearly demonstrated that they are taken up effectively by cells to exert in vivo activity. None of the compounds were toxic to the mice at the highest dose tested.

The $LD_{50}$ values of the most active compounds 14, 25, and 28 in mice were also determined. As such, $N^7$-acyclic nucleoside 14 and butenolide ester derivatives 25 and 28 were administered at different doses intraperitoneally. They did not show any toxicity up to a concentration level as high as 400 mg/kg. All mice were controlled in good conditions after six months of administration. Nevertheless, $LD_{50}$ (i.p.) values of 950 mg/kg, 675 mg/kg, and 710 mg/kg were determined for 14, 25, and 28, respectively. Moreover, no discernible abnormality was observed in the histological appearance of the viscera of either the control or tested groups of mice that received the drugs i.p. (250 mg/kg/day) for 10 days. Furthermore, there were no physiological changes in their cardiovascular or central nerve systems.

Inhibitory Effects of PMEA 4 and Its Butenolide Ester Derivative 28 on MSV-Induced Tumor Formation in Vivo. The inhibitory effects of the compounds 4 and 28 on the initiation of MSV-induced tumor formation and survival of MSV-induced mice (10–15 animals/group) were evaluated as previously described. See, e.g., Balzarini et al. (1993) *Agents Chemother* 37: 332–338 and references cited therein. Results are summarized in Table 8.

Compounds 4 and 28 were evaluated for their inhibitory effect on MSV-induced tumor formation in $NMR_1$ mice (Table 8). The compounds were administered intraperitoneally (50 mg/kg/day) for two consecutive days. Prodrug 28 exhibited much higher anti-MSV activity than PMEA 4 in vivo. At a dose of 10 mg/kg/day, compound 28 prevented tumor formation in 60% of the MSV-infected mice whereas with compound 4 at the same dosage level, only 19% prevention was observed. In surviving animals treated with 28, about 2 g weight loss was observed. In the case of PMEA-treated mice, the weight loss of the surviving animals was at least two times more.

TABLE 1

Solubility and Lipophilicity of Nucleoside and Nucleotide Analogs

| compound | solubility in water (mg/mL) | log P (1-octanol/water)[a] |
|---|---|---|
| 1 | 2.56 | 0.98 |
| acyclovir 2 | 0.40 | −0.48 |
| ara A 3 | 0.48 | −0.50 |
| PMEA 4 | 1.97 | 0.69 |
| 9 | 0.32 | −0.60 |
| 14 | 4.71 | 1.24 |
| 20 | 2.89 | 0.95 |
| 24 | 3.08 | 0.12 |
| 25 | 5.16 | 1.37 |
| PMEG 27 | 0.36 | 0.14 |
| 28 | 7.42 | 2.09 |
| 29 | 2.05 | 0.79 |

[a]Parition coefficients were calculated as P = [substrate]$_{1\text{-octanol}}$/[substrate]$_{H_2O}$.

TABLE 2

Substrate Activity and Inhibitory Property Against ADA[a]

| Substrate | $K_m$ (□M) | rel. $V_{max}$ | $K_i$ (μM) |
|---|---|---|---|
| 1 | 138.6 | 1.48 × 10⁻² | 140.8 |
| ara A 3 | 42.8 | 1.0 | — |
| PMEA 4 | 427.0 | — | >800 |
| 14 | 198.5 | 1.50 × 10⁻⁶ | 8.3 |
| 20 | >800 | — | >800 |
| 24 | 164.5 | 9.78 × 10⁻² | 99.7 |
| 25 | 635.7 | — | >800 |
| 28 | >800 | — | >800 |

[a]The reaction velocity, V, in μmol/min/mg of the enzyme was determined, and a plot of 1/[S] ([S] = substrate concentration) vs. 1/V was made. Thus, by the method of Lineweaver and Burk, the Michaelis ($K_m$) and maximum velocity constants ($V_{max}$) were determined. For inhibition studies, in addition to ara-A 3, substrate solutions contained 1, 4, 14, 20, 24, 25 or 28 and then $K_i$ was measured for each substrate.

TABLE 3

Phosphorylation of Various Nucleosides and Thymidine with HSV or Vero Cell Thymidine Kinases[a]

| | HSV thymidine kinase | | Vero cell thymidine kinase | |
|---|---|---|---|---|
| Substrate | Km (□M) | rel. Vmax | Km (μM) | rel. Vmax |
| 1 | 2.0 × 10⁴ | <3.0 | >3.0 × 10⁴ | <3.0 |
| acyclovir 2 | 1.5 | 39.2 | 2.2 × 10⁴ | <3.0 |
| ara A 3 | 1.5 × 10⁴ | <3.0 | 1.3 × 10⁴ | <3.0 |
| 9 | 12.8 | 28.0 | 18.3 | 12.0 |
| 14 | 30.0 | <3.0 | >3.0 × 10⁴ | <3.0 |
| 2 + 14 (1:1 w/w) | — | 80.9 | — | <3.0 |
| thymidine | 1.0 | 100.0 | 1.0 | 1.0 × 10² |

[a]Apparent Km values were determined for HSV and Vero cell thymidine kinases from reactions containing 50 mM of Tris-HCl (pH 7.5), 2.0 mM of ATP, 2.0 mM of MgCl₂, 1.0 mg/mL of BSA, 1.5 μM of [C¹⁴]-thymidine, and 198 units of enzymes/mL. The results were compared with those of thymidine. All reactions were performed at 37° C. The radiochemical nucleoside kinase coupled assay was used in the determination of the relative substrate velocities.

TABLE 4

Kinetics of the PRPP Synthetase Reaction with Acyclic Nucleoside Phosphonates 4 and 20, Nucleotide Analog 24, and AMP (21)[a]

| substrate | $K_m$ (mM) | $V_{max}$ (µmol/unit/h) | $K_i$[b] (mM) |
|---|---|---|---|
| PMEA 4 | 1.51 | 0.096 | 3.02 |
| 20 | 4.83 | 0.013 | 16.74 |
| AMP 21 | 0.24 | 14.270 | — |
| 24 | 0.57 | 11.560 | 0.79 |

[a]The PRPP synthetase reaction mixture contained 10.0 mM potassium phosphate buffer (pH 8.0), 5.0 mM $MgCl_2$, 2.5 mM PRPP, an appropriate amount of AMP (21) or test compounds, and 0.04 unit of PRPP synthetase. The formation of ATP, diphosphates of PMEA 4, 20, or 24 was analysed by HPLC according to the method of Balzarini and De Clercq.
[b]Inhibition of AMP phosphorylation by the enzyme was measured in the presence of different substrate (AMP) concentrations and appropriate concentrations of 4, 20, and 24. The reaction mixture was incubated at 37° C. for 15 min with 0.002 unit of PRPP synthetase. The formation of ATP was followed by HPLC using a Partisphere anion exchange column.

TABLE 5

Anti-DNA Virus and Anticellular Activities of Nucleoside and Nucleotide Analogs in Tissue Culture.

| | $IC_{50}$[a] (µg/mL) | | | | | | |
|---|---|---|---|---|---|---|---|
| compound | HSV-1 (KOS) | HSV-2 (G) | TK+VZV (YS) | TK−VZV (YS/R) | HCMV (AD-169) | HeLa cell[b] | Vero cell[b] |
| 1 | 4.5 | 8.4 | 7.0 | 9.0 | 4.8 | 196 | 209 |
| acyclovir 2 | 0.46 | 1.2 | 9.7 | 28 | 32 | 259 | 269 |
| ara A 3 | 8.8 | >128 | >128 | >128 | 27 | 73 | 89 |
| PMEA 4 | 11 | 7.4 | 6.1 | 6.0 | 15 | 146 | 175 |
| 7 | >128 | >128 | >128 | >128 | >128 | 157 | 145 |
| 9 | 1.1 | 2.8 | 13 | 38 | 16 | 114 | 99 |
| 12 | >128 | >128 | >128 | >128 | >128 | 169 | 165 |
| 14 | 0.58 | 0.97 | 1.1 | 0.97 | 1.0 | 472 | 496 |
| 20 | 20 | 13 | 8.5 | 8.0 | 21 | 236 | 246 |
| 24 | 7.0 | 4.1 | 3.8 | 4.2 | 11 | 244 | 236 |
| 25 | 3.0 | 1.9 | 1.7 | 2.0 | 4.1 | 326 | 350 |
| PMEG 27 | 4.6 | 6.3 | 0.040 | 0.060 | 0.35 | 9.1 | 7.0 |
| 28 | 3.7 | 3.0 | 2.0 | 2.4 | 5.4 | 139 | 170 |
| 29 | 0.42 | 0.28 | 0.0070 | 0.0080 | 0.020 | 8.8 | 6.6 |
| 1 + 14[c] | 0.060 | 0.10 | 0.17 | 0.23 | 0.18 | 372 | 388 |
| 2 + 14[c] | 0.010 | 0.020 | 0.49 | 0.71 | 0.06 | 420 | 410 |
| 3 + 14[c] | 0.10 | 1.1 | 0.98 | 1.7 | 0.46 | 280 | 293 |

[a]Compound concentration required to inhibit virus-induced cytopathogenicity by 50% was determined according to an established procedure. $IC_{50}$ values represent the mean of duplicate determinations.
[b]Concentration of the compound required to cause microscopically visible change or disruption in about 50% of the cell sheet.
[c]For 1:1 (W/W) mixtures, $IC_{50}$ in µg/mL refers to known antiviral drugs.

TABLE 6

Inhibitory Effects of Nucleotide Analogs on the Cytopathogenicity of HIV-1 and HIV-2 in MT4 Cells, as well as on the Cytopathogenicity of MSV in CEM Cells and Cellular Toxicity.

| | $IC_{50}$[a] (µg/mL) | | | MT4 | CEM |
|---|---|---|---|---|---|
| compound | HIV-1 (IIIB) | HIV-2 (LAV-2) | MSV | cell[b] | cell[b] |
| PMEA 4 | 4.1 | 3.8 | 2.0 | 274 | 285 |
| 20 | 7.8 | 9.1 | 27 | >300 | >300 |
| 24 | 5.9 | 6.4 | 17 | 298 | >300 |
| 25 | 4.9 | 4.2 | 13 | >300 | >300 |
| PMEG 27 | 16 | 18 | 0.19 | 16 | 12 |
| 28 | 1.4 | 1.0 | 0.93 | 265 | 280 |
| 29 | 6.0 | 7.1 | 0.020 | 14 | 13 |

[a]Inhibitory concentrations ($IC_{50}$) were determined by use of an established procedure and represent the average of duplicate determinations.
[b]Concentration of the compound required to reduce the number of viable uninfected cells by 50%.

TABLE 7

Antiviral Effects of compounds 2, 4, 9, 14, 20, 24, 25, and 28 Against HSV-1-Induced Mortality in NMRI Mice Upon Intraperitoneal Administration[a]

| compound | dose (mg/kg/day) | No. of mice | mean day of symptom initiation (%)[b] | mean day of animal death (%)[c] |
|---|---|---|---|---|
| acyclovir 2 | 250 | 20 | >21 (100%) | >21 (100%) |
| | 150 | 20 | 19.1 ± 1.3 (86%) | >21 (100%) |
| | 100 | 15 | 15.6 ± 1.6 (65%) | 18.9 ± 2.1 (80%) |
| PMEA 4 | 250 | 20 | >21 (100%) | >21 (100%) |
| | 150 | 20 | 18.5 ± 1.9 (80%) | >21 (100%) |
| | 100 | 15 | 14.7 ± 1.4 (56%) | 17.0 ± 1.1 (77%) |

TABLE 7-continued

Antiviral Effects of compounds 2, 4, 9, 14, 20, 24, 25, and 28 Against HSV-1-Induced Mortality in NMRI Mice Upon Intraperitoneal Administration[a]

| compound | dose (mg/kg/day) | No. of mice | mean day of symptom initiation (%)[b] | mean day of animal death (%)[c] |
|---|---|---|---|---|
| 9 | 250 | 20 | 15.1 ± 1.2 (67%) | 18.5 ± 1.0 (90%) |
|   | 150 | 20 | 13.0 ± 1.1 (57%) | 16.0 ± 1.5 (78%) |
|   | 100 | 15 | 10.9 ± 0.6 (48%) | 14.1 ± 0.8 (66%) |
| 14 | 250 | 20 | >21 (100%) | >21 (100%) |
|   | 150 | 20 | 19.9 ± 1.3 (88%) | >21 (100%) |
|   | 100 | 15 | 17.5 ± 2.1 (80%) | 19.8 ± 1.7 (95%) |
| 20 | 250 | 20 | 16.8 ± 2.4 (75%) | 20.0 ± 1.7 (95%) |
|   | 150 | 20 | 15.0 ± 0.9 (62%) | 17.8 ± 1.5 (80%) |
|   | 100 | 15 | 12.8 ± 1.1 (51%) | 15.4 ± 1.3 (70%) |
| 24 | 250 | 20 | >21 (100%) | >21 (100%) |
|   | 150 | 20 | 19.3 ± 1.6 (85%) | >21 (100%) |
|   | 100 | 15 | 16.0 ± 1.7 (70%) | 19.5 ± 1.2 (90%) |
| 25 | 250 | 20 | >21 (100%) | >21 (100%) |
|   | 150 | 20 | >21 (100%) | >21 (100%) |
|   | 100 | 15 | 19.6 ± 1.5 (94%) | >21 (100%) |
| 28 | 250 | 20 | >21 (100%) | >21 (100%) |
|   | 150 | 20 | >21 (100%) | >21 (100%) |
|   | 100 | 15 | >21 (100%) | >21 (100%) |
| Saline | 0 | 20 | 3.38 ± 0.7 (0%) | 9.4 ± 0.6 (0%) |

[a]Mice were inoculated intraperitoneally with HSV-1 (KOS). Treatment was initiated 4 h postinfection and continued for 6 consecutive days. Experiments were terminated at day 21.
[b]Values in parantheses represent percentage of HSV-1-infected mice without symptoms at day 21 postinfection.
[c]Values in parantheses represent percentage of HSV-1-infected mice that were alive at day 21 postinfection.

TABLE 8

Inhibitory Effects of Acyclic Nucleoside Phosphonates 4 and Its Prodrug 28 on MSV-Induced Tumor Formation and Associated Death in NMRI Mice Upon Intraperitoneal Administration[a]

| compound | dose (mg/kg day) | No. of mice | mean day of tumor initiation (%)[b] | mean day of animal death (%)[c] |
|---|---|---|---|---|
| PMEA 4 | 50 | 15 | 12.5 ± 1.6 (84%) | 17.8 ± 2.0 (96%) |
|   | 20 | 15 | 12.0 ± 1.3 (58%) | 15.9 ± 1.7 (76%) |
|   | 10 | 10 | 9.6 ± 1.5 (19%) | 13.0 ± 1.1 (42%) |
| 28 | 50 | 15 | 18.4 ± 1.4 (95%) | >21 (100%) |
|   | 20 | 15 | 17.9 ± 1.7 (80%) | >21 (100%) |
|   | 10 | 10 | 14.0 ± 2.1 (60%) | 18.9 ± 1.8 (97%) |
| control untreated | 0 | 30 | 3.82 ± 0.95 (0%) | 7.8 ± 1.3 (0%) |
| control[d] | 0 | 40 | >21 (100%) | >21 (100%) |

[a]All mice received two injections within two days.
[b]Values in parantheses represent percentage of MSV-infected mice without tumors at day 21 postinfection.
[c]Values in parantheses represent percentage of MSV-infected mice that were alive at day 21 postinfection.
[d]Untreated control group was neither treated with MSV nor with the drugs.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for making compound of formula (IV) comprising reacting a compound of formula (III):

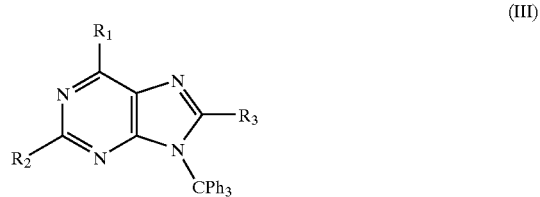

(III)

with an alkyl-X—($CH_2$) halide to obtain a compound of formula (IV):

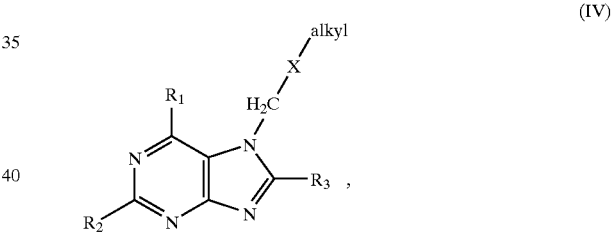

(IV)

in which $R_1$ is $NH_2$ or OH;

$R_2$ is H or $NH_2$;

$R_3$ is H or alkyl; and

X is O, S, or NH;

provided that if $R_1$ is $NH_2$, $R_2$ is H; and if $R_1$ is OH, $R_2$ is $NH_2$.

2. The method of claim 1, wherein $R_1$ is $NH_2$ and $R_2$ is H.

* * * * *